(12) United States Patent
Bonnet et al.

(10) Patent No.: US 8,975,468 B2
(45) Date of Patent: Mar. 10, 2015

(54) DISEASE RESISTANT TOMATO PLANTS

(75) Inventors: Gregori Bonnet, Sarrians (FR); Laurent Grivet, Saint-Sauveur (FR); Bernard Smets, Sarrians (FR)

(73) Assignee: Syngenta Participations AG, Basel (CH)

( * ) Notice: Subject to any disclaimer, the term of this patent is extended or adjusted under 35 U.S.C. 154(b) by 54 days.

(21) Appl. No.: 13/391,153

(22) PCT Filed: Aug. 13, 2010

(86) PCT No.: PCT/EP2010/061858
§ 371 (c)(1),
(2), (4) Date: May 8, 2012

(87) PCT Pub. No.: WO2011/020797
PCT Pub. Date: Feb. 24, 2011

(65) Prior Publication Data
US 2012/0222151 A1 Aug. 30, 2012

(30) Foreign Application Priority Data
Aug. 17, 2009 (EP) .................................. 09167980

(51) Int. Cl.
*A01H 1/04* (2006.01)
*C12Q 1/68* (2006.01)
*C12N 15/82* (2006.01)
*A01H 5/08* (2006.01)

(52) U.S. Cl.
CPC .............. *C12N 15/8282* (2013.01); *A01H 5/08* (2013.01)
USPC ........................ 800/267; 800/265; 800/317.4

(58) Field of Classification Search
None
See application file for complete search history.

(56) References Cited

U.S. PATENT DOCUMENTS

2009/0126037 A1* 5/2009 Finkers et al. ............... 800/265

FOREIGN PATENT DOCUMENTS

EP 1849871 10/2007
EP 1849871 A1 * 10/2007

OTHER PUBLICATIONS

Slate (2005) Molecular Ecology, 14 363-379.*
Finkers Richard et al: "The construction of a *Solanum habrochaites* LYC4 introgression line population and the identification of QTLs for resistance to *Botrytis cinerea*", Theoretical and Applied Genetics, Springer, Berlin, DE, vol. 114, No. 6, Apr. 1, 2007, pp. 1071-1080.
Richard Finkers et al: "Three QTLs for *Botrytis cinerea* resistance in tomato", Theoretical and Applied Genetics; International Journal of Plant Breeding Research, Springer, Berlin, DE, vol. 114, No. 4, Nov. 30, 2006, pp. 585-593.
Richard Finkers: "The genetics of *Botrytis cinerea* resistance in tomato", Apr. 3, 2007, Retrieved from the Internet: URL:http://library.wur.nl/wds/dissertations/dis4162.pdf [retrieved on Dec. 21, 2010].
Richard Finkers et al: "Quantitative resistance to *Botrytis cinerea* from *Solanum neorickii*", Euphytica, Kluwer Academic Publishers, DO, vol. 159, No. 1-2, Jun. 7, 2007, pp. 83-92.
Arjen Ten Have et al: "Partial stem and leaf resistance against the fungal pathogen *Botrytis cinerea* in wild relatives of tomato", European Journal of Plant Pathology, Kluwer Academic Publishers, DO, vol. 117, No. 2, Dec. 23, 2006, pp. 153-166.
Suliman-Pollatschek Saskia et al: "Generation and mapping of AFLP, SSRs and SNPs in *Lycopersicon esculentum*.", Cellular & Molecular Biology Letters 2002, vol. 7, No. 2A, 2002, pp. 583-597.
He C et al: "Development and characterization of simple sequence repeat (SSR) markers and their use in determining relationships among *Lycopersicon esculentum* cultivars.", TAG. Theoretical and Applied Genetics. Theoretische Und Angewandte Genetik Jan. 2003, vol. 106, No. 2, Jan. 2003, pp. 363-373.

* cited by examiner

*Primary Examiner* — David T Fox
*Assistant Examiner* — Steven Bernacki
(74) *Attorney, Agent, or Firm* — Karen A. Magri

(57) ABSTRACT

The present invention relates to cultivated tomato plants that are resistant to the pathogenic fungus *Botrytis cinerea*, which is controlled by at least one QTL, particularly by 2 and 3 QTL contributing to said resistance, wherein said QTL are mapping to linkage group 6, and/or linkage group 1b and/or linkage group 9b. The invention further relates to methods for producing said plants, and to the use thereof.

3 Claims, 3 Drawing Sheets

| QTL | linkage group | TRAIT | MODEL | position (cM) | LOD | a | R2 | 2-LOD confidence interval (cM) |
|---|---|---|---|---|---|---|---|---|
| BCT6.1 | 6 | lg(ls) | CIM | 38 | 10,7 | -0,07 | 14% | 31-41 |
| | | | SIM | 36 | 9,3 | -0,09 | 19% | 31-41 |
| | | ls | CIM | 34 | 9,1 | -4,23 | 11% | 29-41 |
| | | | SIM | 38 | 7,9 | -4,89 | 15% | 31-40 |
| BCT1.1 | 1a | lg(ls) | CIM | 6 | 5,3 | 0,08 | 8% | 0-14 |
| | | | SIM | 6 | 7,1 | 0,09 | 15% | 0-14 |
| | | ls | CIM | 6 | 6,4 | 6,39 | 10% | 0-14 |
| | | | SIM | 4 | 9,2 | 7,06 | 23% | 0-12 |
| BCT1.2 | 1b | lg(ls) | CIM | 48 | 9,9 | -0,06 | 14% | 29-57 |
| | | | SIM | 42 | 12,2 | -0,08 | 24% | 29-56 |
| | | ls | CIM | 52 | 7,7 | -3,04 | 10% | 27-57 |
| | | | SIM | 40 | 11,5 | -4,94 | 21% | 30-57 |
| BCT9.1 | 9b | lg(ls) | CIM | 0 | 6,0 | -0,03 | 7% | 0-6 |
| | | | SIM | 0 | 3,0 | -0,03 | 6% | 0-8 |
| | | ls | CIM | 0 | 6,4 | -2,36 | 7% | 0-6 |
| | | | SIM | 0 | 2,9 | -1,96 | 6% | 0-8 |

*FIG. 3*

DISEASE RESISTANT TOMATO PLANTS

This application is a 371 of International Application No. PCT/EP2010/061858 filed Aug. 13, 2010, which claims priority to EP 09167980.3 filed Aug. 17, 2009, the contents of which are incorporated herein by reference.

The present invention relates to tomato plants, particularly to cultivated tomato plants that are resistant to the pathogenic fungus *Botrytis cinerea*, to methods for producing said plants, and to the use thereof.

*Botrytis* blight, commonly known as gray mold, causes a variety of plant diseases including damping-off and blights of flowers, fruits, stems, and foliage of many vegetables and ornamentals. It is a major cause of postharvest rot of perishable plant produce, including tomatoes at harvest and in storage. The disease can occur both in the greenhouse and in the field.

Gray mold is caused by the fungus *Botrytis cinerea*. One-celled spores are borne on branched conidiophores, from which the spores are liberated to get airborne. The fungus often establishes itself on injured tissues and can persist as a saprophyte for long periods. Stem lesions on seedling tomatoes can occur at, or just below, the soil level. Stems can become infected through leaf scars, dead leaves, or any form of stem damage. Stem lesions often partially girdle the stem, but sometimes the whole stem is affected and the plant is killed. In green houses, *Botrytis* infection is of particular importance. Indeed for undeterminate tomatoes that need to be tutored, the removal of lateral leaves accompanying the growing of the plant always leads to lesions on the stem and such lesions constitute multiple entry points for the pathogen. Petiole lesions appear very similar to those on the stem and often result from infection and colonization of a leaflet. Leaflet lesions often start from senescent tissue or any physical or chemical damage. The more lesions are present on the plant, the more the plant risks to be affected by *Botrytis cinerea*.

In the field the fungus appears as a gray, velvety covering of spores on dying flowers and on the calyx of fruit. Immature green fruit turn light brown or white, starting at the point where they touch other infected plant parts. A soft rot may develop with the fruit skin remaining intact, but the inner tissue becomes mushy and watery. Later, a gray fuzzy mold develops, and sclerotia may appear. Green fruit can also become infected directly by airborne spores instead of by contact with other infections.

There is no known resistance to *B. cinerea* in tomato cultivars.

In Nicot et al ("Differences in susceptibility of pruning wounds and leaves to infection by *Botrytis cinerea* among wild tomato accessions" (Nicot, P. C., 2 Moretti A., 1 Romiti, C., 1 Bardin, M., 2 Caranta C., 1 Ferriére H. INRA—Report of the Tomato Genetics Cooperative Number 52—September 2002)), about 20 wild tomato accessions were evaluated for *Botrytis cinerea* resistance, particularly on stem and leaf lesions. When comparing these 20 accessions with *Solanum lycopersicum* a reduction of symptoms was observed, especially for accessions *L. chmielewski* 731089 and *L. chilense* LA7969. However, Nicot et al do not report identification or introgression of any genetic determinant related to this resistance.

In greenhouse operations, effective control can be achieved by preventing predisposing conditions (high relative humidity and cool temperatures), by adequate spacing and pruning to promote ventilation, by careful handling to prevent wounding, and by removing inoculum sources through adequate plant sanitation.

In the field, this fungus is difficult to control because it causes infections that remain dormant in the field and develop into fruit decay during post-harvest storage. Crop losses of up to 50% are not uncommon. Chemical strategies for controlling *Botrytis* are limited due to the high genetic variability of the fungus which leads to the emergence of strains that are resistant to one or several groups of fungicides. Most fungicides registered for use on tomato are protective in their action and will not suppress an established infection, which limits effective control to pre-harvest applications of fungicides.

There was therefore a long felt and unmet need for convenient, efficient and economically sustainable strategies to protect tomato plants against *Botrytis cinerea* infestation.

The present invention addresses this need by providing a tomato plant, particularly a cultivated tomato plant, which is resistant to *Botrytis cinerea* and thus protected from damage caused by this pathogen. The provision of *Botrytis* resistant tomato plants is an environmentally friendly alternative for the use of pesticides and may increase the efficiency of biological control options and contribute to successful integrated pest management programs.

The technical problem underlying the present invention is, therefore, the provision of a *Botrytis* resistant tomato plant, which shows resistance to this pathogen.

The technical problem is solved by the provision of the embodiments characterized in the claims. In particular, the technical problem was solved by providing a tomato plant exhibiting resistance to *Botrytis cinerea*, said plant comprising at least one genetic determinant directing or controlling expression of said resistance to *Botrytis cinerea* in the tomato plant, wherein said genetic determinant is obtainable from a wild tomato source, particularly from *Solanum habrochaites*, particularly from *Solanum habrochaites* 04TEP990312, seed of which has been deposited under Deposit Number NCIMB 41623. Moreover, it was now surprisingly found within the scope of the present invention that the linkage between genes responsible for undesired, morphological changes at the plant and the gene responsible for the resistance to *Botrytis cinerea* as present in the wild-type source material, such as, for example, in *Solanum habrochaites*, could be broken and is, therefore, no longer present in the tomato plant according to the invention.

(1) In a $1^{st}$ embodiment, the invention relates to a tomato plant, particularly a cultivated tomato plant, exhibiting resistance to *Botrytis cinerea*, said plant comprising at least one genetic determinant directing or controlling expression of said resistance to *Botrytis cinerea* in the tomato plant, wherein the genetic determinant(s) map(s) to at least one linkage group selected from linkage group 6, linkage group 1b and linkage group 9b.

(2) In particular, in a specific embodiment, said genetic determinant is represented by at least one QTL or a functional part thereof capable of directing or controlling expression of said resistance to *Botrytis cinerea*.

(3) In a further specific embodiment of the invention, said QTL or a functional part thereof maps to at least one linkage group selected from linkage group 6, linkage group 1b and linkage group 9b.

(4) In one embodiment, a tomato plant according to embodiment (2) is provided, particularly a cultivated tomato plant, wherein said QTL or a functional part thereof is genetically linked to at least one marker locus, which co-segregates with the *Botrytis* resistance trait and can be identified in a PCR reaction by at least one pair of PCR oligonucleotide primers comprising i. forward primer of SEQ ID NO: 1 and reverse primer of SEQ ID NO: 2, or;
ii. forward primer of SEQ ID NO: 3 and reverse primer of SEQ ID NO: 4, or;
iii. forward primer of SEQ ID NO: 5 and reverse primer of SEQ ID NO: 6, or;
iv. forward primer of SEQ ID NO: 7 and reverse primer of SEQ ID NO: 8, or;
v. forward primer of SEQ ID NO: 9 and reverse primer of SEQ ID NO: 10; or;
vi. forward primer of SEQ ID NO: 11 and reverse primer of SEQ ID NO: 12, or;

by any adjacent marker in at least one linkage group selected from linkage group 6, linkage group 1b and linkage group 9b that is statistically correlated and thus co-segregates with the *Botrytis* resistance trait.

(5) In one embodiment, a tomato plant, particularly a cultivated tomato plant, according to any of the preceding embodiments is provided, wherein said QTL or a functional part thereof is genetically linked to at least two marker loci flanking said QTL or a functional part thereof, which flanking marker loci can be identified in a PCR reaction
i. by a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4, and/or;
ii. by a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8, and/or;
iii. by a $1^{st}$ pair of PCR oligonucleotide primers comprising forward primer of SEQ ID NO: 9 and reverse primer of SEQ ID NO: 10; and a $2^{nd}$ pair of PCR primers comprising forward primer of SEQ ID NO: 11 and reverse primer of SEQ ID NO: 12, and/or;

by an adjacent marker in at least one linkage group selected from linkage group 6, linkage group 1b and linkage group 9b that is statistically correlated and thus genetically linked to the *Botrytis* resistance trait.

(6) In one embodiment of the invention, a tomato plant, particularly a cultivated tomato plant, according to any of the preceding embodiments is provided, wherein said QTL or a functional part thereof maps to linkage group 6 and is flanked by DNA markers represented by a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4.

(7) In one embodiment of the invention, a tomato plant, particularly a cultivated tomato plant, according to any of the preceding embodiments is provided, wherein said QTL or a functional part thereof maps to linkage group 1b and is flanked by DNA markers represented by a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8.

(8) In one embodiment of the invention, a tomato plant, particularly a cultivated tomato plant, according to any of the preceding embodiments is provided, wherein said QTL or a functional part thereof maps to linkage group 9b and is flanked by DNA markers represented by a $1^{st}$ pair of PCR oligonucleotide primers comprising forward primer of SEQ ID NO: 9 and reverse primer of SEQ ID NO: 10; and a $2^{nd}$ pair of PCR primers comprising forward primer of SEQ ID NO: 11 and reverse primer of SEQ ID NO: 12.

(9) In one embodiment of the invention, a tomato plant, particularly a cultivated tomato plant, according to any of the preceding embodiments is provided, wherein said QTL or a functional part thereof maps to linkage group 9b and can be identified in a PCR reaction by a DNA marker represented by a $1^{st}$ pair of PCR oligonucleotide primers comprising forward primer of SEQ ID NO: 9 and reverse primer of SEQ ID NO: 10.

(10) In one embodiment, the invention relates to a tomato plant, particularly a cultivated tomato plant, according to any of the preceding embodiments, comprising at least one allele at a quantitative trait locus in the tomato genome contributing to resistance to *Botrytis cinerea*, which is genetically linked to at least one marker locus, which co-segregates with the *Botrytis cinerea* resistance trait and can be identified in a PCR reaction by at least one pair of PCR oligonucleotide primers comprising
i. forward primer of SEQ ID NO: 1 and reverse primer of SEQ ID NO: 2, or;
ii. forward primer of SEQ ID NO: 3 and reverse primer of SEQ ID NO: 4, or;
iii. forward primer of SEQ ID NO: 5 and reverse primer of SEQ ID NO: 6, or;
iv. forward primer of SEQ ID NO: 7 and reverse primer of SEQ ID NO: 8, or;
v. forward primer of SEQ ID NO: 9 and reverse primer of SEQ ID NO: 10; or;
vi. forward primer of SEQ ID NO: 11 and reverse primer of SEQ ID NO: 12, or;

by any adjacent marker in at least one linkage group selected from linkage group 6, linkage group 1b and linkage group 9b that is statistically correlated and thus co-segregates with the *Botrytis* resistance trait.

(11) In one embodiment, the invention relates to a tomato plant, particularly a cultivated tomato plant, according to any of the preceding embodiments, comprising at least one allele at a quantitative trait locus in the tomato genome contributing to resistance to *Botrytis cinerea*, which is complementary to the corresponding allele present in *Solanum habrochaites*, line 04TEP990312, seed of which is deposited under Deposit Number NCIMB 41623, or in the progeny or in an ancestor thereof, and genetically linked to a least one marker locus in the genome of *Solanum habrochaites*, line 04TEP990312, NCIMB 41623, or in the progeny or in an ancestor thereof, which marker locus co-segregates with the *Botrytis cinerea* resistance trait and can be identified in the genome of *Solanum habrochaites*, line 04TEP990312, NCIMB 41623, or in the progeny or in an ancestor thereof, in a PCR reaction by at least one pair of PCR oligonucleotide primers comprising
i. forward primer of SEQ ID NO: 1 and reverse primer of SEQ ID NO: 2, or;
ii. forward primer of SEQ ID NO: 3 and reverse primer of SEQ ID NO: 4, or;
iii. forward primer of SEQ ID NO: 5 and reverse primer of SEQ ID NO: 6, or;
iv. forward primer of SEQ ID NO: 7 and reverse primer of SEQ ID NO: 8, or;
v. forward primer of SEQ ID NO: 9 and reverse primer of SEQ ID NO: 10; or;
vi. forward primer of SEQ ID NO: 11 and reverse primer of SEQ ID NO: 12, or;

by any adjacent marker in at least one linkage group selected from linkage group 6, linkage group 1b and linkage group 9b that is statistically correlated and thus co-segregates with the *Botrytis* resistance trait.

(12) In one embodiment of the invention, a tomato plant, particularly a cultivated tomato plant, according to any of the preceding embodiments is provided, wherein said QTL or a functional part thereof maps to linkage group 6 and is flanked by DNA markers represented by a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4, further comprising a second QTL that contributes to *Botrytis cinerea* resistance, or a *Botrytis cinerea* resistance-conferring part thereof, wherein said second QTL(2) maps to linkage group 1b and is defined by flanking DNA markers represented by a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8

(13) In one embodiment of the invention, a tomato plant, particularly a cultivated tomato plant, according to any of the preceding embodiments is provided, wherein said QTL or a functional part thereof maps to linkage group 6 and is flanked by DNA markers represented by a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4, further comprising a second QTL that contributes to *Botrytis cinerea* resistance, or a *Botrytis cinerea* resistance-conferring part thereof, wherein said second QTL(2) maps to linkage group 1b and is defined by flanking DNA markers represented by a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8, further comprising a third QTL that contributes to *Botrytis cinerea* resistance, or a *Botrytis cinerea* resistance-conferring part thereof, wherein said third QTL(3) maps to linkage group 9b and is defined by DNA marker represented by a $1^{st}$ pair of PCR oligonucleotide primers comprising forward primer of SEQ ID NO: 9 and reverse primer of SEQ ID NO: 10; and/or adjacent marker represented by a $2^{nd}$ pair of PCR primers comprising forward primer of SEQ ID NO: 11 and reverse primer of SEQ ID NO: 12.

(14) In one embodiment of the invention, a tomato plant, particularly a cultivated tomato plant, according to any of the preceding embodiments is provided, wherein said at least one QTL is obtainable from a donor plant having the genetic background of *Solanum habrochaites* 04TEP990312, seed of which has been deposited under Deposit Number NCIMB 41623, or in the progeny or in an ancestor thereof, comprising said at least one QTL or a *Botrytis cinerea* resistance-conferring part thereof.

(15) In one embodiment, a tomato plant, particularly a cultivated tomato plant, according to any of the preceding embodiments is provided, wherein said genetic determinant is obtainable from *Solanum habrochaites* 04TEP990312, seed of which has been deposited under Deposit Number NCIMB 41623.

(16) In one embodiment of the invention, the tomato plant, particularly a cultivated tomato plant, is a plant according to embodiment (15), wherein said resistance QTL provides a monogenic and dominant resistance to *Botrytis cinerea*.

(17) In one embodiment of the invention, the tomato plant is a plant according to any of the preceding embodiments, which plant is a tomato plant of the genus *Solanum lycopersicum*, particularly (18) a cultivated tomato plant, particularly (19) a haploid, a di-haploid, an inbred or a hybrid.

(20) In one embodiment, the invention provides a plant according to any of the preceding embodiments, which is a hybrid tomato plant, particularly a cultivated tomato plant, comprising at least one QTL or a *Botrytis cinerea* resistance-conferring part thereof, which is genetically linked to at least one marker locus co-segregating with the *Botrytis* resistance trait, wherein said at least one QTL is obtainable from a donor plant having the genetic background of *Solanum habrochaites* 04TEP990312, seed of which has been deposited under Deposit Number NCIMB 41623, or in the progeny or in an ancestor thereof, comprising said at least one QTL or a *Botrytis cinerea* resistance-conferring part thereof.

(21) In one embodiment the tomato plant, particularly a cultivated tomato plant, of the invention is a plant according to any of the preceding embodiments, which grows fruits selected from the group consisting of slicing or globe tomatoes, cherry tomatoes, beefsteak tomatoes, and plum tomatoes.

(22) The present invention further relates to seed of a tomato plant, particularly a cultivated tomato plant, according to any of the preceding embodiments, which is capable of growing a *Botrytis cinerea* resistant tomato plant according to the invention.

(23) In another embodiment, a kit for the detection of the *Botrytis cinerea* resistance locus in a tomato plant, particularly a cultivated tomato plant, is herein provided, wherein said kit comprises at least one PCR oligonucleotide primer, particularly a PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; SEQ ID NO: 10, SEQ ID NO: 11, and SEQ ID NO: 12, or a pair of PCR oligonucleotide primers, selected from
a. primer pair 1 represented by a forward primer of SEQ ID NO: 1 and a reverse primer of SEQ ID NO: 2,
b. primer pair 2 represented by a forward primer of SEQ ID NO: 3 and a reverse primer of SEQ ID NO: 4,
c. primer pair 3 represented by a forward primer of SEQ ID NO: 5 and a reverse primer of SEQ ID NO: 6;
d. primer pair 4 represented by a forward primer of SEQ ID NO: 7 and a reverse primer of SEQ ID NO: 8;
e. primer pair 5 represented by a forward primer of SEQ ID NO: 9 and a reverse primer of SEQ ID NO: 10; and
f. primer pair 6 represented by a forward primer of SEQ ID NO: 11 and a reverse primer of SEQ ID NO: 12; or
another primer representing an adjacent marker in at least one linkage group selected from linkage group 6, linkage group 1b and linkage group 9b that is statistically correlated and thus co-segregates with the *Botrytis* resistance trait.

(24) In one embodiment, a DNA marker is provided that is linked to the *Botrytis cinerea* resistance locus in a tomato plant, particularly a cultivated tomato plant, and can be amplified by at least one oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; SEQ ID NO: 10, SEQ ID NO: 11, and SEQ ID NO: 12, or by a pair of PCR oligonucleotide primers, selected from a. primer pair 1 represented by a forward primer of SEQ ID NO: 1 and a reverse primer of SEQ ID NO: 2,
b. primer pair 2 represented by a forward primer of SEQ ID NO: 3 and a reverse primer of SEQ ID NO: 4,
c. primer pair 3 represented by a forward primer of SEQ ID NO: 5 and a reverse primer of SEQ ID NO: 6;
d. primer pair 4 represented by a forward primer of SEQ ID NO: 7 and a reverse primer of SEQ ID NO: 8;
e. primer pair 5 represented by a forward primer of SEQ ID NO: 9 and a reverse primer of SEQ ID NO: 10; and
f. primer pair 6 represented by a forward primer of SEQ ID NO: 11 and a reverse primer of SEQ ID NO: 12; or by an other primer representing an adjacent marker in at least one linkage group selected from linkage group 6, linkage group 1b and linkage group 9b that is statistically correlated and thus co-segregates with the *Botrytis* resistance trait.

(25) In a further embodiment, the present invention relates also to the use of some or all of these DNA markers according to the invention for diagnostic selection of the *Botrytis cinerea* resistance locus in a tomato plant, particularly a cultivated tomato plant, particularly of the *Botrytis cinerea* resistance locus in at least one linkage group selected from linkage group 6, linkage group 1b and linkage group 9b, particularly in a tomato plant according to the invention.

(26) In another embodiment, the present invention further contemplates the use of some or all of these DNA markers for identifying in a tomato plant, particularly a cultivated tomato plant, particularly a tomato plant according to the invention, the presence of the *Botrytis cinerea* resistance locus and/or for monitoring the introgression of the *Botrytis cinerea* resistance locus in a tomato plant, particularly a cultivated tomato plant, particularly a *Solanum lycopersicum* plant, particularly a tomato plant according to the invention and as described herein.

(27) In one embodiment, the invention relates to the polynucleotide (amplification product) obtainable in a PCR reaction involving at least one oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; SEQ ID NO: 10, SEQ ID NO: 11, and SEQ ID NO: 12, or a pair of PCR oligonucleotide primers, selected from
a. primer pair 1 represented by a forward primer of SEQ ID NO: 1 and a reverse primer of SEQ ID NO: 2,
b. primer pair 2 represented by a forward primer of SEQ ID NO: 3 and a reverse primer of SEQ ID NO: 4,
c. primer pair 3 represented by a forward primer of SEQ ID NO: 5 and a reverse primer of SEQ ID NO: 6;
d. primer pair 4 represented by a forward primer of SEQ ID NO: 7 and a reverse primer of SEQ ID NO: 8;
e. primer pair 5 represented by a forward primer of SEQ ID NO: 9 and a reverse primer of SEQ ID NO: 10; and
f. primer pair 6 represented by a forward primer of SEQ ID NO: 11 and a reverse primer of SEQ ID NO: 12; or by an other primer representing an adjacent marker in at least one linkage group selected from linkage group 6, linkage group 1b and linkage group 9b that is statistically correlated and thus co-segregates with the *Botrytis* resistance trait, which amplification product corresponds to an amplification product obtainable from *Solanum habrochaites* 04TEP990312, seed of which has been deposited under Deposit Number NCIMB 41623, in a PCR reaction with identical primers or primer pairs provided that the respective marker locus is still present in said tomato plant and/or can be considered an allele thereof.

(28) In a specific embodiment, the invention relates to an amplification product according to embodiment (27) obtained in a PCR reaction using
i. a primer pair comprising forward primer of SEQ ID NO: 1 and reverse primer of SEQ ID NO: 2, which leads to an amplification product, which is in a range of between 205 bp and 235 bp, particularly of between 210 bp and 230 bp; particularly of between 215 bp and 225 bp and/or is between 10% and 20%, particularly between 12% and 18%, particularly about 14% shorter than the corresponding fragment obtainable from a susceptible *S. lycopersicum* elite line, particularly line W5016;
ii. a primer pair comprising forward primer of SEQ ID NO: 3 and reverse primer of SEQ ID NO: 4, which leads to an amplification product, which is in a range of between 224 bp and 226 bp, and/or is between 0.4% and 1.8%, particularly between 0.8% and 1.5% longer than the corresponding fragment obtainable from a susceptible *S. lycopersicum* elite line, particularly line W5016;
iii. a primer pair comprising forward primer of SEQ ID NO: 5 and reverse primer of SEQ ID NO: 6, which leads to an amplification product, which is in a range of between 160 bp and 170 bp, particularly of between 162 bp and 168 bp; particularly of between 164 bp and 166 bp and/or is between 3% and 10%, particularly between 5% and 9%, particularly about 6% shorter than the corresponding fragment obtainable from a susceptible *S. lycopersicum* elite line, particularly line W5016;
iv. a primer pair comprising forward primer of SEQ ID NO: 7 and reverse primer of SEQ ID NO: 8, which leads to an amplification product, which is in a range of between 85 bp and 95 bp, particularly of between 88 bp and 92 bp; and/or is between 5% and 15%, particularly between 8% and 12%, particularly about 11% shorter than the corresponding fragment obtainable from a susceptible *S. lycopersicum* elite line, particularly line W5016;
v. a primer pair comprising forward primer of SEQ ID NO: 9 and reverse primer of SEQ ID NO: 10, which leads to an amplification product, which is in a range of between 290 bp and 320 bp, particularly of between 280 bp and 310 bp; and/or is between 5% and 15%, particularly between 8% and 12%, particularly about 10% shorter than the corresponding fragment obtainable from a susceptible *S. lycopersicum* elite line, particularly line W5016;
vi. a primer pair comprising forward primer of SEQ ID NO: 11 and reverse primer of SEQ ID NO: 12, which leads to an amplification product, which is in a range of between 140 bp and 160 bp; particularly of between 145 bp and 155 bp and/or is between 10% and 30%, particularly between 15% and 25%, particularly about 20% shorter than the corresponding fragment obtainable from a susceptible *S. lycopersicum* elite line, particularly line W5016.

(29) Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the *Botrytis cinerea* resistance locus.

(30) The present invention therefore further relates in one embodiment to derived markers, particularly to derived primers or probes, developed from an amplification product according to the invention and as described herein above by methods known in the art, which derived markers are genetically linked to the *Botrytis cinerea* resistance locus, particularly the *Botrytis cinerea* resistance locus in at least one linkage group selected from linkage group 6, linkage group 1b and linkage group 9b.

(31) These derived markers can then by used to identify *Botrytis cinerea* resistant plants, wherein the markers specifically disclosed herein are recombined relative to the resistance and thus no longer present in the resistant plant genome.

(32) In a further embodiment, a method is provided within the present invention for introducing at least one allele associated with resistance to *Botrytis cinerea* at a quantitative trait locus contributing to resistance to *Botrytis cinerea* into a tomato plant, particularly a cultivated tomato plant, lacking said allele comprising: a) obtaining a first tomato plant according to any one of the preceding embodiments; b) crossing said first tomato plant with a second tomato plant, wherein said second tomato plant lacks said allele; and c) identifying a plant resulting from the cross exhibiting increased resistance to *Botrytis cinerea* and comprising at least one marker allele co-segregating with said *Botrytis cinerea* resistance; and d) optionally, isolating said plant and e) optionally, back-crossing said plant with the first or second tomato plant.

(33) In a further embodiment, the invention relates to a method for producing a tomato plant, particularly a cultivated tomato plant, exhibiting resistance to *Botrytis cinerea*, comprising the steps of:
a. selecting a plant of the genus *Solanum*, which exhibits *Botrytis cinerea* resistance, wherein said resistance is associated with at least one QTL or a functional part thereof capable of directing or controlling expression of said resistance to *Botrytis cinerea*, wherein said QTL or a functional part thereof is genetically linked to at least one marker locus, which co-segregates with the *Botrytis* resistance trait and can be identified in a PCR reaction by at least one pair of PCR oligonucleotide primers comprising
 i. forward primer of SEQ ID NO: 1 and reverse primer of SEQ ID NO: 2, or;
 ii. forward primer of SEQ ID NO: 3 and reverse primer of SEQ ID NO: 4, or;
 iii. forward primer of SEQ ID NO: 5 and reverse primer of SEQ ID NO: 6, or;
 iv. forward primer of SEQ ID NO: 7 and reverse primer of SEQ ID NO: 8, or;
 v. forward primer of SEQ ID NO: 9 and reverse primer of SEQ ID NO: 10; or;
 vi. forward primer of SEQ ID NO: 11 and reverse primer of SEQ ID NO: 12, or;
 by any adjacent marker in at least one linkage group selected from linkage group 6, linkage group 1b and linkage group 9b that is statistically correlated and thus co-segregates with the *Botrytis* resistance trait;
b. crossing said plant of step a), which exhibits *Botrytis cinerea* resistance, with a tomato plant, particularly a cultivated tomato plant, which is susceptible to *Botrytis cinerea* or exhibits an intermediate level of resistance against *Botrytis cinerea*, and
c. selecting progeny from said cross which exhibits *Botrytis* resistance and demonstrates association with said at least one marker locus of step a).

(34) In one embodiment, the invention relates to a method for producing a tomato plant, particularly a cultivated tomato plant, exhibiting resistance to *Botrytis cinerea*, comprising the steps of:
a. selecting a plant of the genus *Solanum*, which exhibits *Botrytis cinerea* resistance, wherein said resistance is associated with at least one QTL or a functional part thereof capable of directing or controlling expression of said resistance to *Botrytis cinerea*, wherein said QTL or a functional part thereof is genetically linked to at least two marker loci flanking said QTL or a functional part thereof, which flanking marker loci can be identified in
 i. a PCR reaction with a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4, and/or
 ii. a PCR reaction with a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8, and/or
 iii. a PCR reaction with a $1^{st}$ pair of PCR oligonucleotide primers comprising forward primer of SEQ ID NO: 9 and reverse primer of SEQ ID NO: 10; and a $2^{nd}$ pair of PCR primers comprising forward primer of SEQ ID NO: 11 and reverse primer of SEQ ID NO: 12, or
 by an adjacent marker in at least one linkage group selected from linkage group 6, linkage group 1b and linkage group 9b that is statistically correlated and thus genetically linked to the *Botrytis* resistance trait and
b. crossing said plant of step a), which exhibits *Botrytis cinerea* resistance, with a tomato plant, particularly a cultivated tomato plant, which is susceptible to *Botrytis cinerea* or exhibits an intermediate level of resistance against *Botrytis cinerea*, and
c. selecting a progeny from said cross which exhibits *Botrytis* resistance and demonstrates association with said at least two marker loci of step a).

(35) In one embodiment of the invention, a method according to embodiment 33 is provided for obtaining a tomato plant, particularly a cultivated tomato plant, resistant to *Botrytis cinerea*, wherein the donor plant of step (a) comprises a QTL contributing to resistance to *Botrytis cinerea*, wherein said QTL or a functional part thereof maps to linkage group 6 and is flanked by DNA markers represented by a $1^{st}$ pair of PCR oligonucleotide primers comprising forward primer of SEQ ID NO: 1 and reverse primer of SEQ ID NO: 2, and a $2^{nd}$ pair of PCR primers comprising forward primer of SEQ ID NO: 3 and reverse primer of SEQ ID NO: 4. In particular, said *Solanum* donor plant of step (a) is *Solanum habrochaites* (36).

(37) In one embodiment, a method according to any one of the preceding embodiments is provided for obtaining a tomato plant, particularly a cultivated tomato plant, resistant to *Botrytis cinerea*, wherein the donor *Solanum* plant of step (a) is a tomato plant according to any one of the preceding embodiments, (38) the method comprising the additional step of backcrossing the *Botrytis* resistant tomato plant obtained in step c) with the susceptible tomato plant of step b).

(39) In one embodiment, the determination of the association between *Botrytis* resistance and the at least one marker locus or the at least two marker loci in step c) of the method according to any of the preceding embodiments is accomplished by carrying out a PCR reaction with the primers identified in step a).

(40) In a further embodiment, the invention provides a method for obtaining tomato fruits resistant to *Botrytis cinerea* comprising the steps of
  i. sewing a seed of a plant according to any one of embodiments 1 to 22 or obtained in a method according to any of the preceding embodiments; and
  ii. growing said plant in order to produce fruit and harvesting the fruits produced by said plant.
(41) In still another embodiment, the invention relates to a *Botrytis cinerea* resistance-conferring QTL or a *Botrytis cinerea* resistance-conferring part thereof, which maps to linkage group 6 of plant accession NCIMB 41623, and is associated with at least a $1^{st}$ DNA marker represented by a $1^{st}$ pair of PCR oligonucleotide primers comprising forward primer of SEQ ID NO: 1 and reverse primer of SEQ ID NO: 2, and/or a at least a $2^{nd}$ DNA marker represented by a $2^{nd}$ pair of PCR primers comprising forward primer of SEQ ID NO: 3 and reverse primer of SEQ ID NO: 4, particularly (42) said QTL or a functional part thereof is flanked by said $1^{st}$ and $2^{nd}$ DNA marker.
(43) In still another embodiment, the invention relates to a *Botrytis cinerea* resistance-conferring QTL or a *Botrytis cinerea* resistance-conferring part thereof, which maps to linkage group 1b of plant accession NCIMB 41623, and is associated with at least a $1^{st}$ DNA marker represented by a $1^{st}$ pair of PCR oligonucleotide primers comprising forward primer of SEQ ID NO: 5 and reverse primer of SEQ ID NO: 6, and a $2^{nd}$ pair of PCR primers comprising forward primer of SEQ ID NO: 7 and reverse primer of SEQ ID NO: 8, particularly (41) said QTL or a functional part thereof is flanked by said $1^{st}$ and $2^{nd}$ DNA marker.
(44) In a further embodiment, the invention relates to a *Botrytis cinerea* resistance-conferring QTL or a *Botrytis cinerea* resistance-conferring part thereof, which maps to linkage group 9b of plant accession NCIMB 41623, and is associated with at least a $1^{st}$ DNA marker represented by a $1^{st}$ pair of PCR oligonucleotide primers comprising forward primer of SEQ ID NO: 9 and reverse primer of SEQ ID NO: 10; and/or adjacent marker represented by a $2^{nd}$ pair of PCR primers comprising forward primer of SEQ ID NO: 11 and reverse primer of SEQ ID NO: 12, particularly (45) said QTL or a functional part thereof is flanked by said $1^{st}$ and $2^{nd}$ DNA marker.
(46) The present invention also relates to the use of *Botrytis cinerea* resistant propagating material obtainable from a tomato plant according to any of the preceding embodiments for growing a *Botrytis* resistant plant in order to produce fruit and harvest said fruits.
(47) In still another embodiment, in invention provides a method of protecting a crop of tomato plants, particularly cultivated tomato plants, against infection by *Botrytis cinerea*, wherein said method is characterized by planting a seed according to embodiment 22, and growing a tomato plant, particularly a cultivated tomato plant, which exhibits a resistance against *Botrytis cinerea*, in particular, (48) said tomato plant or crop is sprayed with a crop protection chemical active against *Botrytis cinerea* at a lower concentration or less frequently than a tomato crop not exhibiting said resistance.
(49) In one embodiment, the invention relates to a method of producing hybrid seed s of a tomato plant, particularly a cultivated tomato plant, resistant to *Botrytis* comprising the steps of:
  i. planting a male-sterile female plant or line, and a male-fertile plant or line, wherein at least one of said male or female plants or lines is a plant according to any of embodiments 1 to 21,
  ii. effecting cross pollination between both lines,
  iii. growing the progeny plant till fruit setting,
  iv. collecting the fruits and
  v. obtaining the hybrid seeds.
(50) In a specific embodiment, the invention relates to a method for producing hybrid seeds of tomato plant, particularly a cultivated tomato plant, resistant to *Botrytis* comprising the steps of:
  i. planting a male-sterile female plant or line, and a male-fertile plant or line, wherein at least one of said male or female plants or lines is a plant according to any of the preceding embodiments,
  ii. effecting cross pollination between both lines,
  iii. selecting a progeny from said cross which exhibits *Botrytis* resistance and demonstrates association with said at least one marker locus of step a) using at least one of the markers disclosed herein;
  iv. growing the progeny plant selected in iii) till fruit setting,
  v. collecting the fruits and
  vi. obtaining the hybrid seeds.

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated tomato" plant is understood within the scope of the invention to refer to a plant that is no longer in the natural state but has been developed by human care and for human use and/or growing purposes and/or consumption. "Cultivated tomato plants" are further understood to exclude those wild-type species which comprise the trait being subject of this invention as a natural trait and/or part of their natural genetics.

A "genetic determinant directing or controlling expression" is understood herein to refer to a heritable genetic element that is capable of contributing to the resistance of the plant towards the pathogen by influencing expression of this resistance trait on the level of the DNA itself, on the level of translation, transcription and/or activation of a final polypeptide product, i.e., to down regulate and counter the infestation leading to the phenotypic expression of the resistance.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the quantitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic marker can be physically located in a position on a chromosome that is within or outside of to the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the term "linkage group" refers to a set of genes, alleles or loci that tend to be transmitted and to segregate together and usually belong to a given chromosome. In most cases, a given linkage group X corresponds to chromosome X. Accordingly, within the scope of the present invention linkage group 6 corresponds to chromosome 6, linkage groups 1a and 1b correspond to chromosome 1 and linkage group 9b corresponds to chromosome 9.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen pressure, e.g. fungus.

As used herein, the phrase "susceptibility" refers to the inability of a plant to adequately restrict the growth and development of a specified pathogen.

As used herein, the phrase "*Botrytis*" resistance" or "resistance to *Botrytis cinerea*" or "*Botrytis* resistant plant" refers to the plants capability to resist colonization by the fungus.

*Botrytis* resistance is determined within the scope of the present invention in a pathotest as described in detail in Example 1.1 below.

The pathotest is designed such that the resulting evidenced resistance is as close as possible to the real-life commercial conditions of tomato cultivation. In particular, the resistance manifests itself on the stem of the plant, where the leaf was pruned and the cut leave inoculated with *Botrytis mycelium*. This assessment of resistance is mimicking the conditions of infestation of tomato plant in the green houses by the *Botrytis* pathogen, where the growers continuously cut and remove lateral leaves in order to facilitate tutoring and harvesting as well as for balanced plant vigor and plant productivity.

Furthermore, the resistance testing according to the present invention is done with a number of aggressive and very aggressive *Botrytis* strains, which have been developed from a collection of different strains isolates (see table 2). Isolates have been characterized based on morphology and the ITS sequences of ribosomal DNA (rDNA).

A plant is qualified as a "*Botrytis* resistant plant" if a core collection of strains such as that shown in table 2, which is virulent to a susceptible *S. lycopersicum* elite line in a pathotest according to Example 1, showing different levels of aggressiveness evidenced by stem lesions of various length, particularly stem lesions of between 15 mm and 50 mm in length, failed to develop stem lesions on the test-plant of any significance, that is stem lesions of less than 6 mm, particularly of less than 5 mm in length.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes). In the present case the quantitative trait exhibits continuous variation between individuals of a population in terms of resistance to a fungus of the genus Botrytis, particularly Botrytis cinerea, which resistance is scored by means of a standardized Resistance Assay using the length of necrotic lesions around the infestation site for assessing the severity of the infestation.

A quantitative trait (QTL) is typically the result of a genetic locus interacting with the environment or of multiple genetic loci interacting with each other and/or with the environment. Examples of quantitative traits include plant height and yield.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "co-segregation" also refers to the presence of two or more traits within a single plant of which at least one is known to be genetic and which cannot be readily explained by chance.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, fruit color, and several known disease resistances such as, for example, Fungus spot resistance, Fusarium Wilt resistance or Tomato Mosaic Virus resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus Solanum used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the melting temperature ($T_m$) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The terms "race" or "races" refer to any inbreeding group, including taxonomic subgroups such as subspecies, taxonomically subordinate to a species and superordinate to a subrace and marked by a pre-determined profile of latent factors of hereditary traits.

As used herein, the term "population" means a genetically heterogeneous collection of plants sharing a common genetic derivation As used herein, the term "tomato" means any variety, cultivar, or population of *Solanum lycopersicum* var. *cerasiforme, Solanum pimpinellifolium, Solanum cheesmaniae, Solanum neorickii, Solanum chmielewskii, Solanum habrochaites, Solanum pennellii, Solanum peruvianum, Solanum chilense, S. lycopersicoides, S. N peruvianum, S. corneliomuelleri, S. 'Callejon de Huaylas', S. galapagense* a.d *S. sitiens*. and *Solanum lycopersicum*.

As used herein, the term "variety" or "cultivar" means a group of similar plants that by structural features and performance can be identified from other varieties within the same species.

In one embodiment, the present invention relates to novel *Botrytis* resistant tomato plants and tomato lines, and improved methods for producing them utilizing the molecular markers described herein in selective breeding techniques. More specifically, the present invention provides certain novel *Botrytis* resistant tomato plants wherein said resistance is controlled by at least one QTL. Tomato plants that do not contain at least one of the QTLs identified herein are susceptible to infection by *Botrytis*.

In particular, the at least one QTL controlling the *Botrytis* resistance is located on chromosome 1, 6 and 9, respectively.

The invention thus relates in one embodiment to a tomato plant exhibiting resistance to *Botrytis cinerea*, said plant comprising at least one non-native genetic determinant directing or controlling expression of said resistance to *Botrytis cinerea* in the tomato plant, wherein said non-native genetic determinant(s) originates from a wild tomato species or a progenitor thereof and map(s) to at least one linkage group selected from linkage group 6, linkage group 1b and linkage group 9b.

Molecular markers located on said chromosomes and co-segregating with the *Botrytis* resistance can be identified using marker-assisted selection, the techniques for which are well known in the art. Markers that can be used in such selection techniques are represented by at least one oligonucleotide primer selected from the group of primers given in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, by any adjacent marker in at least one linkage group selected from linkage group 6, linkage group 1b and linkage group 9b that is statistically correlated and thus co-segregates with the *Botrytis* resistance trait. One source of a *Botrytis* resistant tomato plant that contains the hereinbefore described QTLs on chromosome 1, 6 and 9, respectively, is *Solanum habrochaites*, line 04TEP990312, NCIMB 41623, seed of which has been deposited under Deposit Number NCIMB 41623. Other related tomato plants that exhibit resistance to *Botrytis* and contain one or more QTLs that encode for *Botrytis* resistance can now be identified by using one or more of the markers provided herein.

Moreover, other accessions of related tomato species can now be examined for the presence of at least one of the QTLs identified herein by using the markers of the present invention including, without being limited to, *Solanum lycopersicum* var. *cerasiforme*, *Solanum pimpinellifolium*, *Solanum cheesmaniae*, *Solanum neorickii*, *Solanum chmielewskii*, *Solanum habrochaites*, *Solanum pennellii*, *Solanum peruvianum*, *Solanum chilense*, *S. lycopersicoides*, *S. N peruvianum*, *S. comeliomuelleri*, *S. 'Callejon de Huaylas'*, *S. galapagense* a.d *S. sitiens*. and *Solanum lycopersicum*.

The molecular markers provided herein and co-segregating with at least one QTL located on chromosome 1, 6 and 9, respectively, contributing to *Botrytis* resistance, may be used to introgress one or more of said QTL or a functional part thereof from a first donor plant into a second recipient plant.

The recipient plant is preferably a tomato plant, particularly a cultivated tomato plant, particularly a cultivated *Solanum lycopersicum*, carrying one or more traits of agronomic importance such as, for example,
a. holding ability of the fruit on the plant, i.e., firm fruit walls and thick skin, no decay of older fruits, no germination of seeds in the older fruits, no breakdown of sugars inside the older fruits, and no fermentation within the older fruit;
b. firmness of the fruits to withstand mechanical harvesting and transportation as well as storage under open sky conditions at 38° C. without significant breakdown and disease development;
c. firmness of the fruits to withstand high pressure steam (e.g., 15-30 psi at 105°-120° C.) and/or application of chemicals (e.g., 11-19% NaOH at 85°-99° C.) to peel the skin off the fruits;
d. firmness of the fruits to withstand high pressure steam for cooking as whole tomatoes;
e. firmness of the fruits to withstand cutting to make diced tomato products; and
f. firmness of the sliced and diced tomato products to withstand cooking with high pressure steam.

Tomato plants developed according to the present invention can advantageously derive a majority of their traits from the recipient plant, and derive *Botrytis* resistance from the first donor plant. According to one aspect of the present invention, genes that encode for *Botrytis* resistance are mapped by identifying molecular markers linked to resistance quantitative trait loci, the mapping utilizing a mix of resistant and susceptible to *Botrytis* inbred tomato plants for phenotypic scoring. Molecular characterization of such lines can be conducted using the techniques described by Monforte and Tanksley in Genome, 43: 803-813 (2000). By example, and not of limitation, the association between the *Botrytis*-resistant phenotype and marker genotype can be investigated using the software package QTLCartographer (C J Basten, P Gaffney, Z B Zeng, North Carolina State University, 2006).

In another embodiment of the present invention, the present invention relates to methods for producing superior new *Botrytis* resistant tomato plants. In the method of the present invention, one or more genes encoding for *Botrytis* resistance are introgressed from a donor parental plant that is resistant to *Botrytis* into a recipient tomato plant that is either non-resistant or a plant that has intermediate levels of resistance to infection by *Botrytis*. The *Botrytis* resistant tomato plants produced according to the methods of the present invention can be either inbred, hybrid, or haploid tomato plants.

The introgression of one or more genes encoding for *Botrytis* resistance into a recipient tomato plant that is non-resistant or possesses intermediate levels of resistance to *Botrytis* can be accomplished using techniques known in the art. For example, one or more genes encoding for *Botrytis* resistance can be introgressed into a recipient tomato plant that is non-resistant or a plant that has intermediate levels of resistance to *Botrytis* using traditional breeding techniques.

The tomato plants according to the present invention and as described herein can be used in commercial tomato seed production. Commercial tomatoes are generally hybrids produced from the cross of two parental lines (inbreds). The development of hybrids requires, in general, the development of homozygous inbred lines, the crossing of these lines, and the evaluation of the crosses.

Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes and characteristics. The new inbreds are crossed with other inbred lines and the hybrids from these crosses are evaluated to determine which of those have commercial potential. Plant breeding and hybrid development are expensive and labour and time-consuming processes.

Pedigree breeding starts with the crossing of two genotypes, each of which may have one or more commercially desirable characteristics, such as, but not limited to, disease resistance, insect resistance, valuable fruit characteristics, increased yield, etc. that is lacking in the other or which complements the other. If the two original parents do not provide all the desired characteristics, other sources can be included in the breeding population in order to generate an established breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc. A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid performance (hybrid vigor or heterosis), can be manifested in many polygenic traits, including increased vegetative growth and increased yield. Tomato plants can be easily cross-pollinated. A trait is also readily transferred from one tomato plant to another plant, including tomato plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait, particularly the "*Botrytis* resistance" trait according to the present invention. The progeny of this cross is then mated back to the recurrent parent followed by selection in the resultant progeny for the trait. After three, preferably four, more preferably five or more generations of backcrosses with the recurrent parent with selection for the trait, particularly the "*Botrytis* resistance" trait according to the present invention, the progeny is heterozygous for the locus harbouring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross. Male sterility is available in tomato. In particular genetic male sterility may be used in commercial lines. e.g., sweet tomato lines (see for example Alexander Kilchevsky and Michail Dobrodkin, Acta Physiologiae Plantarum Volume 22, Number 3/September 2000).

The population can be screened in a number of different ways. First, the population can be screened using a traditional pathology disease screen. Such pathology disease screens are known in the art. Specifically, the individual plants or parts thereof can be challenged in a climatic chamber or a greenhouse with *Botrytis* and the resulting resistant or susceptible phenotypes of each plant scored.

By way of example, and not of limitation, plants can be screened in a climatic chamber at a day temperature of between 20° C. and 24°, particularly at 22° C. with a luminosity of between 4000 and 6000 lux, particularly 5000 lux, and a night temperature of between 16° C. and 20° C., particularly 18° C.

The evaluation of the symptoms is assessed based on the length of stem necrosis, which usually develops about 2 to 4 days, particularly 3 days after inoculation. Necrosis assessment is carried out about 6 to 8 days, particularly 7 days after inoculation. For each line, a mean of length necrosis is recorded from each plant from each experiment.

Particularly for the evaluation of lines and hybrids, plants can be screened in semi-artificial conditions close to market production facilities under greenhouse conditions. Seeds are sown in trays with suitable substrate, for example adapted compost, for sowing. Trays are incubated in climatic chambers with a photoperiod of 15 h/9 h (day/night). The day temperature is between 22° C. and 26°, particularly 24° C. with a luminosity of between 8000 and 12000 lux, particularly 10000 lux, and a night temperature of between 16° C. and 20° C., particularly 18° C.

Seedlings are transplanted in pots with suitable substrate, for example adapted compost, about 8 to 12 days, particularly 10 days after sowing. After 3 to 5 weeks, particularly after 4 weeks, seedlings were transplanted directly in soil in a greenhouse.

Spore inoculation may be carried out after about 1.5 to 3 month, particularly 2 months of growth. 2 to 3 leaves of each plant are pruned. A $1 \times 10^5$ to $1 \times 10^7$ spores/ml water solution, particularly a $1 \times 10^6$ spores/ml water solution, optionally comprising 10% sucrose (weight/volume) may be used as an inoculum. The inoculum is spread immediately after pruning, on the wounded part. A second followed by a third inoculation is performed each 2 to 4 weeks, particularly each 3 weeks with the same protocol. After several weeks, on the susceptible reference (the *Solanum lycopersicum* elite line) necrosis can be observed which resulted in plant death. Symptoms assessment may be done by counting the number of dead plants per plot and by measuring the biggest necrosis length of each plant from each plot once at least 50% of the susceptible plants have died. For each line or hybrid, a mean of necrosis length is recorded.

Second, marker-assisted selection can be performed using one or more of the hereinbefore described molecular markers to identify those hybrid plants that contain one or more of the genes that encode for *Botrytis* resistance. Alternatively, marker assisted selection can be used to confirm the results obtained from the pathology screen. F2 hybrid plants exhibiting a *Botrytis* resistant phenotype contain the requisite genes encoding for *Botrytis* resistance, and possess commercially desirable characteristics, are then selected and selfed for a number of generations in order to allow for the tomato plant to become increasingly inbred. This process of continued selfing and selection can be performed for five or more generations. The result of such breeding and selection is the production of lines that are genetically homogenous for the genes associated with *Botrytis* resistance as well as other genes associated with traits of commercial interest. Alternatively, a new and superior *Botrytis* resistant inbred tomato plant line can be developed using the techniques of recurrent selection and backcrossing. In this method, *Botrytis* resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has an intermediate level of resistance to *Botrytis* and possesses commercially desirable characteristics, such as, but not limited to disease resistance, insect resistance, valuable fruit characteristics, etc.

The non-recurrent parent exhibits *Botrytis* resistance and contains one or more genes that encode for *Botrytis* resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. First, the population can be screened using a traditional pathology screen as described previously herein. Second, marker-assisted selection can be performed using one or more of the hereinbefore described molecular markers to identify those progeny that contain one or more of genes encoding for *Botrytis* resistance. Alternatively, marker-assisted selection can be used to confirm the results obtained from the pathology screen. Once the appropriate selections are made, the process is repeated. The process of backcrossing to the recurrent parent and selecting for *Botrytis* resistance is repeated for approximately five or more generations. The progeny resulting from this process are heterozygous for one or more genes that encode for *Botrytis* resistance. The last backcross generation is then selfed in order to provide for homozygous pure breeding progeny for *Botrytis* resistance. The *Botrytis* resistant inbred tomato lines described herein can be used in additional crossings to create *Botrytis* resistant hybrid plants. For example, a first *Botrytis* resistant inbred tomato plant can be crossed with a second inbred tomato plant possessing commercially desirable traits such as, but not limited to, disease resistance, insect resistance, desirable fruit characteristics, etc. This second inbred tomato line may or may not be resistant to *Botrytis*. The marker-assisted selection used in the hereinbefore described methods can be made, for example, step-wise, whereby the different *Botrytis* resistant genes are selected in more than one generation; or, as an alternative example, simultaneously, whereby all resistance genes are selected in the same generation. Marker-assisted selection for *Botrytis* resistance may be done before, in conjunction with, or after testing and selection for other commercially desirable traits such as disease resistance, insect resistance, desirable fruit characteristics, etc.

In particular, marker-based selection may be applied in combination with or followed by a phenotypic selection to identify those individuals where all of the invention relevant loci described herein before have homozygous favourable genotypes.

There are several types of molecular markers that may be used in marker-based selection including, but not limited to, restriction fragment length polymorphism (RFLP), random amplification of polymorphic DNA (RAPD), amplified restriction fragment length polymorphism (AFLP), single sequence repeats (SSR) and single nucleotide polymorphisms SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Alternative methods may be employed to amplify fragments, such as the "Ligase Chain Reaction" ("LCR") (Barany, Proc. Natl. Acad. Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, a molecular marker is a DNA fragment amplified by PCR, e.g. a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif. Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants.

In the present invention a marker or a set of two or more markers may be used comprising a pair of PCR oligonucleotide primers comprising i. forward primer of SEQ ID NO: 1 and reverse primer of SEQ ID NO: 2, or;
ii. forward primer of SEQ ID NO: 3 and reverse primer of SEQ ID NO: 4, or;
iii. forward primer of SEQ ID NO: 5 and reverse primer of SEQ ID NO: 6, or;
iv. forward primer of SEQ ID NO: 7 and reverse primer of SEQ ID NO: 8, or;
v. forward primer of SEQ ID NO: 9 and reverse primer of SEQ ID NO: 10; or;
vi. forward primer of SEQ ID NO: 11 and reverse primer of SEQ ID NO: 12, which primers lead to an amplification product in a PCR reaction exhibiting a molecular weight or a nucleotide sequence, which is essentially identical or can be considered as an allele to that of a corresponding PCR amplification product obtainable from *Solanum habrochaites*, line 04TEP990312, NCIMB 41623 in a PCR reaction with the identical primer pair(s); or; any adjacent marker in at least one linkage group selected from linkage group 6, linkage group 1b and linkage group 9b that is statistically correlated and thus co-segregates with the *Botrytis* resistance trait.

In one embodiment of the invention, said amplification product is substantially different in length from that obtainable from a susceptible *S. lycopersicum* elite line, particularly line W5016.

In particular, the amplification product is obtained in a PCR reaction using i. a primer pair comprising forward primer of SEQ ID NO: 1 and reverse primer of SEQ ID NO: 2, which leads to an amplification product, which is in a range of between 205 bp and 235 bp, particularly of between 210 bp and 230 bp; particularly of between 215 bp and 225 bp and/or is between 10% and 20%, particularly between 12% and 18%, particularly about 14% shorter than the corresponding fragment obtainable from a susceptible *S. lycopersicum* elite line, particularly line W5016;

ii. a primer pair comprising forward primer of SEQ ID NO: 3 and reverse primer of SEQ ID NO: 4, which leads to an amplification product, which is in a range of between 224 bp and 226 bp, and/or is between 0.4% and 1.8%, particularly between 0.8% and 1.5% longer than the corresponding fragment obtainable from a susceptible *S. lycopersicum* elite line, particularly line W5016;

iii. a primer pair comprising forward primer of SEQ ID NO: 5 and reverse primer of SEQ ID NO: 6, which leads to an amplification product, which is in a range of between 160 bp and 170 bp, particularly of between 162 bp and 168 bp; particularly of between 164 bp and 166 bp and/or is between 3% and 10%, particularly between 5% and 9%, particularly about 6% shorter than the corresponding fragment obtainable from a susceptible *S. lycopersicum* elite line, particularly line W5016;

iv. a primer pair comprising forward primer of SEQ ID NO: 7 and reverse primer of SEQ ID NO: 8, which leads to an amplification product, which is in a range of between 85 bp and 95 bp, particularly of between 88 bp and 92 bp; and/or is between 5% and 15%, particularly between 8% and 12%, particularly about 11% shorter than the corresponding fragment obtainable from a susceptible *S. lycopersicum* elite line, particularly line W5016;

v. a primer pair comprising forward primer of SEQ ID NO: 9 and reverse primer of SEQ ID NO: 10, which leads to an amplification product, which is in a range of between 290 bp and 320 bp, particularly of between 280 bp and 310 bp; and/or is between 5% and 15%, particularly between 8% and 12%, particularly about 10% shorter than the corresponding fragment obtainable from a susceptible *S. lycopersicum* elite line, particularly line W5016;

vi. a primer pair comprising forward primer of SEQ ID NO: 11 and reverse primer of SEQ ID NO: 12, which leads to an amplification product, which is in a range of between 140 bp and 160 bp; particularly of between 145 bp and 155 bp and/or is between 10% and 30%, particularly between 15% and 25%, particularly about 20% shorter than the corresponding fragment obtainable from a susceptible *S. lycopersicum* elite line, particularly line W5016.

In a first step, DNA or cDNA samples are obtained from suitable plant material such as leaf tissue by extracting DNA or RNA using known techniques. Primers that flank a region containing SSRs within the invention-relevant qualitative trait locus disclosed herein before or within a region linked thereto, are then used to amplify the DNA sample using the polymerase chain reaction (PCR) method well-known to those skilled in the art.

Basically, the method of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerase. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment that is approximately $2^{<n>}$, where n is the number of cycles.

Through PCR amplification millions of copies of the DNA segment flanked by the primers are made. Differences in the number of repeated sequences or insertions or deletions in the region flanking said repeats, which are located between the flanking primers in different alleles are reflected in length variations of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

In the alternative, the presence or absence of the desired allele may be determined by real-time PCR using double-stranded DNA dyes or the fluorescent reporter probe method.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, a distinction can be made between homozygous plants that carry two copies of the desired, invention-relevant allele at the *Botrytis* resistance quantitative locus and heterozygous plants that carry only one copy and plants that do not contain any copy of the favourable allele(s).

Thus, alternative markers can therefore be developed by methods known to the skilled person and used to identify and select plants with an allele or a set of alleles of a quantitative trait locus or loci according to the present invention and as disclosed herein before.

For example, the nucleotide sequence of the amplification product obtained in PCR amplification using the a pair of PCR oligonucleotide primers comprising i. forward primer of SEQ ID NO: 1 and reverse primer of SEQ ID NO: 2, or;

ii. forward primer of SEQ ID NO: 3 and reverse primer of SEQ ID NO: 4, or;

iii. forward primer of SEQ ID NO: 5 and reverse primer of SEQ ID NO: 6, or;

iv. forward primer of SEQ ID NO: 7 and reverse primer of SEQ ID NO: 8, or;

v. forward primer of SEQ ID NO: 9 and reverse primer of SEQ ID NO: 10; or;

vi. forward primer of SEQ ID NO: 11 and reverse primer of SEQ ID NO: 12, or;

any adjacent marker in at least one linkage group selected from linkage group 6, linkage group 1b and linkage group 9b that is statistically correlated and thus co-segregates with the *Botrytis* resistance trait, can be obtained by those skilled in the art and new primers or primer pairs designed based on the newly determined nucleotide sequence of the PCR amplification product. Furthermore, the markers according to the invention and disclosed herein before could be positioned on a genetic map of tomato or other species, in particular species of the family Solanaceae and known markers mapping in the same or homolog or ortholog region(s) could be used as starting point for developing new markers.

Accordingly, the markers specifically disclosed in the present invention may also be used in the identification and/or development of new or additional markers associated with the *Botrytis* resistance quantitative locus, which in turn can then be used in marker assisted breeding and/or the search of recombinants flanking the *Botrytis* resistance locus, and/or fine-mapping, and/or cloning of the *Botrytis* resistance quantitative locus.

There are several methods or approaches available, known to those skilled in the art, which can be used to identify and/or develop markers in linkage disequilibrium and/or linked to and/or located in the region o interest, as well as markers that represent the actual causal mutations underlying the quantitative trait. Without being fully exhaustive some approaches, known by those skilled in the art, include:

use of disclosed sequences/markers in hybridization approaches to identify other sequence in the region of interest: primer sequences as disclosed herein and/or marker/gene sequences (or part thereof) that can be determined using the primer sequences as disclosed herein may be used as (hybridization) probes in isolating nucleic acid sequences/genes flanking the markers and/or linked and/or associated and/or specific for the *Botrytis* resistance locus from a genomic nucleic acid sample and/or RNA or cDNA sample or pool of samples (for example screening of genomic resources like BAC libraries or gDNA or cDNA library screening).

use of disclosed sequences/markers in PCR approaches to identify other sequence in the region of interest: primer sequences as disclosed herein and/or marker/(candidate) gene sequences (or part thereof) that can be determined using the primer sequences as disclosed may be used as (PCR) amplification primers to amplify a nucleic acid sequence/gene flanking and/or linked to and/or associated with and/or specific for the region of the *Botrytis* resistance locus from a genomic nucleic acid sample and/or RNA or cDNA sample or pool of samples either or not isolated from a specific plant tissue and/or after specific treatment of the plant and from *Solanum* spp. or in principal any other organism with sufficient homology.

use of disclosed sequences/markers in PCR approaches to identify other sequence in the region of interest: the nucleotide sequences/genes of one or more markers can be determined after internal primers for said marker sequences may be designed and used to further determine additional flanking sequence/genes within the region of the *Botrytis* resistance locus and/or genetically linked and/or associated with the trait.

use of disclosed sequences/markers in mapping and/or comparative mapping approaches to identify markers in the same region(s) (positioning of the *Botrytis* resistance locus on other maps): based on positional information and/or marker information as disclosed herein, markers, of any type, may be identified by genetic mapping approaches, eventually (if already needed) by positioning of the disclosed markers (by genetic mapping or extrapolation based on common markers across maps) on a (high density) genetic map(s), and/or integrated genetic or consensus map(s). Markers already known and/or new markers genetically linked and/or positioned in the vicinity of the disclosed markers and/or the region of the *Botrytis* resistance locus may be identified and/or obtained and eventually used in (fine-) mapping and/or cloning of the *Botrytis* resistance locus and/or MAS applications.

use of disclosed sequences/markers in 'in-silico' approaches to identify additional sequences/markers/(candidate) genes: Primer sequences as disclosed herein and/or marker/(candidate) gene sequences (or part thereof) that can be determined using the primer sequences as disclosed herein or based on linked markers may be used in 'in-silico' methods to search sequence or protein databases (e.g. BLAST) for (additional) flanking and/or homolog sequences/genes and/or allelic diversity (both genomic and/or cDNA sequences or even proteins and both originating from *Solanum* spp. and/or any other organism) genetically linked and/or associated with the traits as described herein and/or located in the region of the *Botrytis* resistance locus.

use of disclosed sequences/markers in physical mapping approaches (positioning of the *Botrytis* resistance locus on physical map or genome sequence): primer sequences as disclosed herein and/or marker/gene sequences (or part thereof) that can be determined using the primer sequences as disclosed herein or using other markers genetically linked to the markers disclosed herein and/or located in the region of the *Botrytis* resistance locus may be positioned on a physical map and/or (whole) genome sequence in principal of any organism with sufficient homology to identify (candidate) sequences/markers/genes applicable in (fine-mapping) and/or cloning of the *Botrytis* resistance locus and/or MAS breeding applications.

use of disclosed sequences/markers to position the *Botrytis* resistance locus on other (physical) maps or genomes (across species . . . for tomato other Solanaceae species may be used as model species): primer sequences as disclosed herein and/or marker/gene sequences (or part thereof) that can be determined using the primer sequences as disclosed herein may be used in comparative genome or syntheny mapping approaches to identify homolog region and homolog and/or ortholog sequences/(candidate) genes genetically linked and/or positioned in the region of the *Botrytis* resistance locus and applicable in (fine-mapping) and/or cloning of the *Botrytis* resistance locus and/or MAS breeding applications.

use of disclosed sequences/markers to select the appropriate individuals allowing the identification of markers in region of interest by genetic approaches: primer sequences and/or markers as disclosed herein may be used to select individuals with different/contrasting alleles which in for example in genetic association approaches and/or bulk segregant analysis (B S A, Michelmore et al., PNAS, 88, 9828-9832, 1991) can be used to identify markers/genes in the specific region of interest and/or associated or genetically linked to the described traits.

use of disclosed information to search for (positional) candidate genes: the disclosed information may be used to identify positional and/or functional candidate genes which may be associated with the described traits and/or genetically linked.

For genotyping, mapping or association mapping, DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire tomato genome.

Joint-analysis of genotypic and phenotypic data can be performed using standard software known to those skilled in the art. Plant introductions and germplasm can be screened for the alleles at the corresponding *Botrytis* resistance locus disclosed herein, based on the nucleotide sequence(s) of the marker(s) at the marker locus/loci linked to said *Botrytis* resistance locus or any other marker, and the molecular weight of the allele(s) using one or more of the techniques disclosed herein or known to those skilled in the art.

The nucleic acid sequence of markers, linked markers or the *Botrytis* resistance locus disclosed herein may be determined by methods known to the skilled person. For example, a nucleic acid sequence comprising said *Botrytis* resistance locus or a resistance-conferring part thereof may be isolated from a *Botrytis* resistant donor plant by fragmenting the genome of said plant and selecting those fragments harbouring one or more markers indicative of said *Botrytis* resistance locus. Subsequently, or alternatively, the marker sequences (or parts thereof) indicative of said resistance locus may be used as (PCR) amplification primers, in order to amplify (a) nucleic acid sequence(s) comprising said resistance locus form a genomic nucleic acid sample or a genome fragment obtained from said plant. The nucleotide sequence of the *Botrytis* resistance locus, and/or of any additional marker comprised therein, may be obtained by standard sequencing methods.

The present invention therefore also relates to an isolated nucleic acid (preferably DNA but not limited to DNA) sequence that comprises a *Botrytis* resistance locus of the present invention, or a resistance-conferring part thereof. Thus the markers discloses may be used for the identification and isolation of one or more markers or genes from tomato or other vegetable crops, particularly Solanaceae crops that are linked or encode *Botrytis* resistance.

The nucleotide sequence of additional markers linked to the *Botrytis* resistance locus of the present invention may for instance also be resolved by determining the nucleotide sequence of one or more markers associated with the *Botrytis* resistance locus and designing primers for said marker sequences that may then be used to further determine the sequence outside of said marker sequence. For example the nucleotide sequence of the SSR markers disclosed herein or any other markers predicted in the region of the *Botrytis* resistance locus and/or linked to said region may be obtained by sequencing the PCR amplification product of said markers by methods well known in the art. Or alternatively using the marker sequences in a PCR or as hybridization probes to identify linked nucleotide sequences by for example, but not limited to, BAC screening.

The present invention is further described by reference to the following non-limiting figures, tables and examples.

Figure 1:
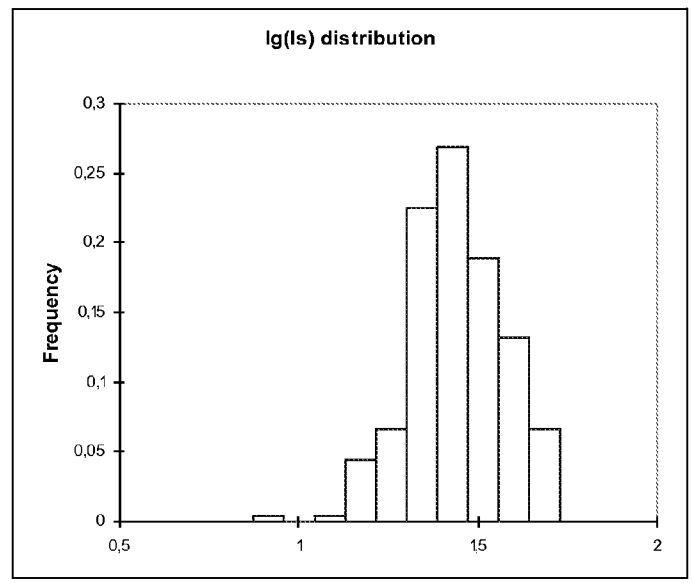
FIG. 1 shows the distribution of the two traits that have been used to detect QTLs for *Botrytis* tolerance in the F4 RIL population (derived from cross between line A and line B).
Figure 1:
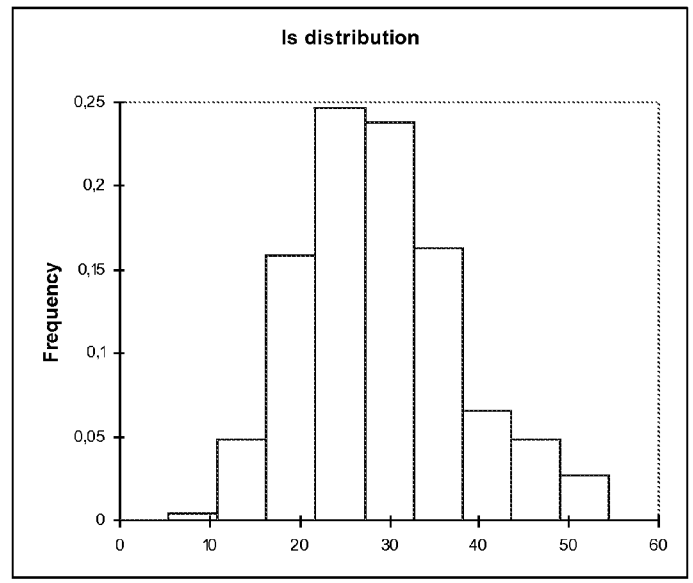

FIG. 3 shows QTL detected in the F4 Recombinant Inbred Line population derived from cross between line A and line B for tolerance to *Botrytis cinerea*. Traits for which QTL detection has been performed are lesion size (Is) and the logarithm of lesion size (lg(Is)). Each QTL is named with prefix BcT (for *Botrytis cinerea* tolerance) followed by the number of the chromosome and a distinctive numeral.

The foregoing description will be more fully understood with the reference to the following Examples. Such Examples are, however, exemplary methods of practising the present invention and are not intended to limit the scope of the invention. The following Examples illustrate the invention:

EXAMPLES

Materials
1. *Bortytis*—Resistance Source Material

Resistance to *Botrytis* was identified in and obtained from *S. habrochaites* accession PI 247087. For this accession the following source history can be provided:

Accession was collected in. Ecuador, 1 Jan. 1958.

Locality: on the bank between Catamayo and Gonzanama, Hacienda Colca, Loja.

Collectors: Correll, D., Crops Research Division—USDA-ARS.

Accession was donated. 9 Apr. 1958. Maryland, United States.

Donors: Correll, D., Crops Research Division—USDA-ARS. Maintained by the Northeast Regional PI Station. USDA, ARS, National Genetic Resources Program, 630 W. North Street, Geneva, N.Y. NPGS received: 9 Apr. 1958. PI assigned: 1958. Released in 1958.

2. Fungal Strain

An aggressive isolate of *Botrytis cinerea* was used for the phenotypic evaluations of the population for the QTL analysis and also for lines and hybrids. The strain was maintained on Petri dishes with solid Potato Dextrose Agar medium 2% (PDA) under controlled temperature at 20° C. For solid PDA medium, 2 g of PDA was added per liter of water. The material was autoclaved to sterility, cooled, and poured onto Petri dishes.

A monthly subculture was made from a small piece of agar containing mycelium into a new sterile Petri dish.

3. Climatic Chambers Evaluation—Inoculation with Mycelium

Active cultures were obtained after 5 days under controlled temperature at 20° C. A piece of agar, containing mycelium, was taken with the base of a tip generally use with a micro pipette. The tip is used as a "carry part". The tip containing the mycelium is placed on the remaining part of a cut leave in contact with the stem.

4. Plastic Greenhouse Evaluation—Inoculation with Fungus Spore Solution

From a new Petri dish, spores appear from the mycelium after 4 weeks. Spores are collected from the Petri dish by removing the fungus with a scalpel and put in a water solution. The mycelium containing spores was mixed in the water solution with a mixer and a count was done with a Mallassez cell. The water spore solution was diluted to $1.10^6$ spores/ml.

The inoculation was carried out with a spore solution with 10% sucrose (weight/volume).

Example 1

Pathotest Screening 1.1 *Botrytis* Strain Collection

A core collection has been built from a collection of strains isolated in 2004 and 2005. Isolates have been characterized based on morphology and the ITS sequences of rDNA.

The core collection has been chosen according to strain morphology in Petri Dish on PDA medium (Fabian et al, 2003).

1.2 BC2F4 Lines Population Evaluation

Seeds were sown in trays with adapted compost for sowing. Trays were incubated in climatic chambers with a photoperiod of 15 h/9 h (day/night). The temperature during the days was 24° C.±2° C. with a luminosity of 10 000 lux and during the night the temperature was 18° C.±2° C.

Seedlings are transplanted in pots with adapted compost about 10 days after sowing. Seedlings were grown in climatic chambers until the fifth or sixth true leave under similar conditions. Seedlings are watered each day after transplantation with a nutritive solution until the inoculation (Liquoplant Bleu from Plantin, Courthezon, France; with the following NPK composition: 2.5 (whole nitrogen)–5 (P2O5)–2.5 (K2O)–0.75 (MgO)+oligo-elements. The solution is diluted to obtain an electro-conductivity of 2 and a pH of 6.5).

The inoculation was carried out after 4 weeks of growth. 2 Leaves of each plant are pruned. There is at least one remaining leave between those which have been cut. A 5 days old mycelium is used as inoculum.

A piece of mycelium is placed on the remaining part of the cut leave in contact with the stem. The mycelium was maintained with a tip fitted together with the remaining plant part.

Plants were incubated in climatic chambers under saturated humidity with a temperature during the day 22°±2° C. with a luminosity of 5 000 lux and during the night the temperature was 18° C.±2° C.

The first symptoms, necrosis on the wounded cut plant part, appeared after day 3 post inoculation. The evaluation of symptoms was assessed on the length of the stem necrosis using a quantitative measure in millimetres. The necrosis length is generally assessed after day 7 post inoculation. On the susceptible reference, the necrosis length is generally over 30 mm.

For each line, a mean of length necrosis was recorded from each plant from each experiment.

The climatic chamber was divided in 12 experimental units and could contain 1080 plants.

A number of 6 experiments have been conducted in order to screen the entire population. The elementary experimental unit was a group of 5 F4 plants. 5 resistant and susceptible controls were grown in each experimental unit of the climatic chamber.

1.3 Lines and Hybrids Evaluation in a Breeding Program

In addition of the procedure described above for the QTL study, lines and hybrids were evaluated in semi-artificial conditions close to market production facilities under a plastic greenhouse.

Seeds were sown in trays with adapted compost for sowing. Trays were incubated in climatic chambers with a photoperiod of 15 h/9 h (day/night). The temperature during the days was 24°±2° C. with a luminosity of 10 000 lux and during the night the temperature was 18° C.±2° C.

Seedlings are transplanted in pots with adapted compost about 10 days after sowing. After 4 weeks, seedlings were transplanted directly in soil in a plastic greenhouse.

The inoculation was carried out after 2 months of growth. 2 Leaves of each plant are pruned. A $1\times10^6$ spores/ml water solution with 10% sucrose (weight/volume) was used. The inoculum was spread immediately after pruning, on the wounded part. A second inoculation, followed by a third inoculation was performed each 3 weeks with the same protocol. After several weeks, on the susceptible reference (the *Solanum lycopersicum* elite line) necrosis was observed on the susceptible reference (the *Solanum lycopersicum* elite line), which resulted in plant death. Symptoms assessment was carried out by counting the number of dead plants per plot and by measuring the biggest necrosis length of each plant from each plot once at least 50% of the susceptible plants were dead. For each line or hybrid, a mean of length necrosis was recorded.

Example 2

QTL Mapping Experiment 2.1 QTL Determination

Resistance to *Botrytis* has been identified in *S. habrochaites* accession PI 247087. This accession has been backcrosses once to a susceptible *S. lycopersicum* elite line, and then selfed during 3 generations while selecting the most resistant plant at each generation trough pathotest screening. The same *S. lycopersicum* elite line was used in Example 3 as the susceptible control.

The most resistant BC1F3 plant (parent A) has then been crossed to W5016 (parent B). From this cross a population of 492 F3 lines has been developed by single seed descent. F4 seeds have been obtained from each F3 plant.

A genetic map has been constructed based on the 492 F3 plants with 161 SSR markers. Markers were assembled into 19 linkage groups while 10 markers remained unlinked. 17 linkage groups could be assigned to 10 chromosomes of the tomato genome while 2 remained unidentified.

The F4 line, resulting from the selfing of each F3 plant has been used to characterize the resistance level to *Botrytis cinerea*. The resistance test has been performed in a climatic chamber. The climatic chamber was divided in 12 experimental units and could contain 1080 plants. Plants were inoculated at the 5/6 leaf stage, that is 30 to 40 days after sawing. Each plant was inoculated at 2 different nodes. Resistance was measured as the extension of the necrotic lesion in millimeter, 7 days after inoculation. A number of 6 experiments have been conducted in total in order to screen the entire population. The elementary experimental unit was a group of 5 F4 plants representing the corresponding F3 plant. Each F3 plant has been evaluated through at least two samples of 5 F4 plants. One resistant and one susceptible control were grown in each experimental unit of the climatic chamber.

The length of the necrotic lesion has been measured in millimeters at the two inoculation points of each plant. Then the lesion length has been averaged over all F4 plants and all repetitions of a given F3 plant. Data coming from a given experimental unit were not considered if symptoms were not fully expressed on the susceptible control (average lesion length smaller than 20 mm). The traits used for the QTL detection were the lesion length (Is) and the logarithm of the lesion length (Ig(Is)). The distribution of the two traits is given in FIG. 1.

QTL detection has been performed with the software QTL-Cartographer (C J Basten, P Gaffney, Z B Zeng, North Carolina State University, 2006). The statistical model used for the detection was a composite interval mapping (CIM) model. Option with selection of cofactors through forward and backward regression, with a probability for input and output at p=5% was used. The threshold to consider a QTL as present was LOD=3. QTL summary statistic, that is Lodscore, genetic effect (a) and percentage of variance explained (R2) are given in FIG. 3. The sign of the genetic effect is negative when the resistant allele is inherited from parent A and the sign is positive when it is coming from parent B. The results for simple interval mapping (SIM), another classical QTL detection method, are also given in FIG. 3. A total of 4 QTLs have been detected, in 3 cases, the favourable allele (that is the allele bringing the highest level of resistance that is the smallest necrotic lesion) was the one inherited from parent A, while in one case the favourable allele was inherited from parent B.

The 3 QTLs with resistance effect coming from parent A are:

QTL BCT6.1. The Lodscore peak is between position 34 and 38 cM depending on trait and statistical method, that is between markers NT1293 and NT3736. The percentage of variance explained is between 11% and 14%.

QTL BCT1.2. The Lodscore peak is between position 42 and 52 cM depending on trait and statistical method, that is between markers NT1597 and NT4636. The percentage of variance explained is between 10% and 14%.

QTL BCT9.1. The Lodscore peak is at position 0 cM on marker NT5734. The percentage of variance explained is 7%. The 2-LOD confidence interval includes markers NT5734 and NT5921.

Figure 2:
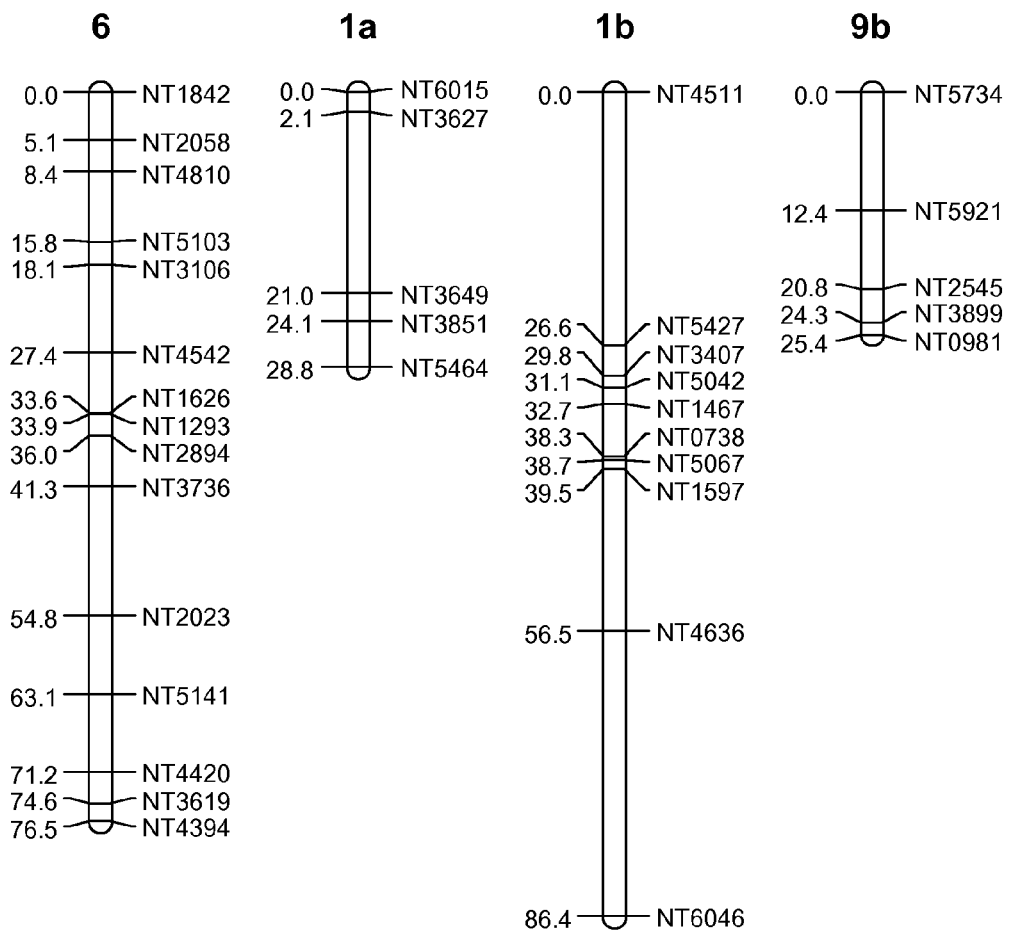
FIG. 2 shows the genetic map of linkage groups where QTL for *Botrytis* tolerance have been detected in the F4 RIL population (derived from cross between line A and line B).

The genetic map of linkage groups 6, 1a, 1b and 9b are given on FIG. 2. Information permitting to genotype these flanking markers is given in table 3.

TABLE 1

Summary of the size of amplicons for the flanking markers

| Marker | R allele from 04TEP990312 (in bp) | S allele from W5016 (in bp) | Precision | Measurement method |
|---|---|---|---|---|
| NT1293 | 220 | 250 | ±7 bp | Agarose gel |
| NT3736 | 225 | 222 | ±1 bp | Sequencer |
| NT1597 | 165 | 175 | ±5 bp | Agarose gel |
| NT4636 | 90 | 100 | ±5 bp | Agarose gel |
| NT5734 | 300 | 330 | ±7 bp | Agarose gel |
| NT5921 | 150 | 180 | ±5 bp | Agarose gel |

Example 3

Results of Lines and Hybrid Evaluation

TABLE 2

Results of the pathotest according to Example 1 on a susceptible *S. lycopersicum* elite line and line 04TEP990312

| Core Collection | Necrosis | | | |
|---|---|---|---|---|
| *B. cinerea* strains | 04TEP990312 | σ | *S. lycopersicum* | σ |
| BcT1 | 4.9 | 3.1 | 49.8 | 14.1 |
| BcT29B | 3.7 | 0.5 | 48.1 | 12.2 |
| BcT7A | 4.6 | 1.6 | 46.1 | 15.5 |
| BcT24 | 3.8 | 0.5 | 42.7 | 10.0 |
| BcT8C | 4.4 | 1.1 | 39.9 | 13.1 |
| BcT5A | 3.9 | 0.3 | 32.3 | 13.6 |
| BcT7C | 3.8 | 0.5 | 31.4 | 16.5 |
| BcT19 | 3.8 | 0.9 | 30.4 | 10.4 |
| BcT10A | 3.4 | 0.3 | 28.6 | 14.5 |
| BcT6E | 3.8 | 0.9 | 25.6 | 13.5 |
| BcF3A2 | 3.9 | 0.5 | 23.6 | 10.9 |
| BcF3A1 | 3.6 | 0.3 | 23.5 | 8.6 |
| BcT6D | 3.8 | 0.8 | 23.1 | 6.1 |
| BcF1 | 4.3 | 0.7 | 23.0 | 10.9 |
| BcT35B | 4.0 | 0.5 | 22.7 | 9.2 |
| BcL3 | 3.8 | 0.5 | 21.5 | 8.7 |
| BcL1A | 5.1 | 3.6 | 17.4 | 4.1 |
| BcL5B | 3.8 | 0.2 | 16.9 | 6.6 |

On the susceptible *S. lycopersicum* elite line, all strains are virulent and show different level of aggressiveness.

On resistant donor line 04TEP990312, all strains failed to develop stem lesions and they could be considered as avirulent on this resistant genotype.

Example 4

Phenotypic Data on Lines Harboring QTL(s)

4.1 $1^{st}$ Experiment:

29 advanced lines BC4F3; previously selected according to their phenotype during each previous cycle; have been genotyped and found fixed for the *Solanum habrochaites* (04TEP990312) introgression for the QTL BCT6.1. These lines have been evaluated together and compared to a susceptible reference, a *Solanum lycopersicum* susceptible elite line (TS) used as recurrent in a backcross program. A resistant reference (TR), a BC2F5 lines harboring the resistance allele at the 3 QTLs (BCT1.2, BCT6.1 and BCT9.1) have been also include in the experiment.

Each line has been evaluated according to the procedure described in the example 1 on 24 plants.

The statistical significance of the Log 10 transformed values of the necrosis length (mm) was evaluated by analysis of variance (ANOVA). Duncan's multiple range test was used to detect significant differences at the 5% significance level between lines carrying the *S. habrochaites* (04TEP990312) introgression for the QTL BCT6.1 and lines without this introgression.

4.1.1 *Botrytis* strain BcT1

| Duncan Grouping | Log10 | N | BCT6.1 |
|---|---|---|---|
| A | 1.57 | 10 | TS |
| B | 1.23 | 10 | TR |
| B | 1.22 | 29 | P |

TS = *S. lycopersicum* susceptible elite line
TR = *S. lycopersicum* resistant reference line
P = BC4F3 lines homozygous for the *S. habrochaites* (04TEP990312) introgression on the QTL BCT6.1

In this experiment, the BC4F3 lines, homozygous for the *S. habrochaites* (04TEP990312) introgression on the QTL BCT6.1, are significantly different from the *S. lycopersicum* susceptible elite line. These lines showed a significant reduction of the necrosis length.

4.2 $2^{nd}$ Experiment:

The following two experiments differ according to the reference *Botrytis cinerea* strains used. In the $1^{st}$ experiment, lines have been challenged with the BcT1 strain and in the $2^{nd}$ experiment, lines have been challenged with the BcT19 strain. Strains differ in their level of aggressiveness.

76 BC4F3 Lines, coming from the same F2 populations, homozygous for the *S. habrochaites* (04TEP990312) introgression or homozygous for *S. lycopersicum* for the QTL BCT6.1, have been selected and compared.

Each line has been evaluated in 2 independent experiments according to the procedure described in the example 1, on 12 plants.

The statistical significance of the Log 10 transformed values of the necrosis length (mm) was evaluated by analysis of variance (ANOVA). Duncan's multiple range test was used to detect significant differences at the 5% significance level between lines carrying the *S. habrochaites* (04TEP990312) introgression for the QTL BCT6.1 and lines without this introgression.

4.2.1 *Botrytis* strain BcT1:

| Duncan Grouping | Log10 | N | BCT6.1 |
|---|---|---|---|
| A | 1.32 | 11 | TS |
| A | 1.24 | 42 | A |
| B | 1.08 | 34 | P |
| C | 0.96 | 11 | TR |

TS = *S. lycopersicum* susceptible elite line
TR = *S. lycopersicum* resistant reference line
A = BC4F3 lines without the *S. habrochaites* (04TEP990312) introgression on the QTL BCT6.1
P = BC4F3 lines homozygous for the *S. habrochaites* (04TEP990312) introgression on the QTL BCT6.1

4.2.2 *Botrytis* strain BcT19::

| Duncan Grouping | Log10 | N | BCT6.1 |
|---|---|---|---|
| A | 1.82 | 11 | TS |
| B | 1.77 | 42 | A |
| C | 1.66 | 34 | P |
| D | 1.33 | 11 | TR |

TS = *S. lycopersicum* susceptible elite line
TR = *S. lycopersicum* resistant reference line
A = BC4F3 lines without the *S. habrochaites* (04TEP990312) introgression on the QTL BCT6.1
P = BC4F3 lines homozygous for the *S. habrochaites* (04TEP990312) introgression on the QTL BCT6.1

In the two independent experiments, there is a significant difference between homozygous lines with and without the *S. habrochaites* (04TEP990312) introgression for the QTL BCT6.1. Lines with the *S. habrochaites* (04TEP990312) introgression showed a significant reduction of the necrosis length.

4.3 $3^{rd}$ Experiment:

The three following experiments differ according to the reference strains used of *Botrytis cinerea*. In the $1^{st}$ and in the $2^{nd}$ experiment, lines have been challenged with the BcT1 strain and in the $3^{rd}$ experiment; lines have been challenged with the BcT19 strain. Strains differ in their level of aggressiveness.

21 BC3F3 lines, coming from the same F2 populations, have been selected according to QTLs BCT1.2 or BCT9.1. These lines harboring at the homozygous stage the QTL BCT1.2 or the QTL BCT9.1 have been compared in three independent experiments with the procedure described in the example 1.

Each line has been tested on 40 plants with 4 replicates of 10 plants. The statistical significance of the Log 10 transformed values of the necrosis length (mm) was evaluated by analysis of variance (ANOVA). Duncan's multiple range test was used to detect significant differences at the 5% significance level between lines carrying one QTL and lines without the corresponding QTL.

4.3.1 *Botrytis* strain BcT1:

| Duncan Grouping | Log10 | N | BCT1.2 |
|---|---|---|---|
| A | 1.69 | 12 | TS |
| A | 1.67 | 12 | A |

4.3.1 *Botrytis* strain BcT1:

| Duncan Grouping | Log10 | N | BCT1.2 |
|---|---|---|---|
| B | 1.53 | 8 | P |
| C | 1.17 | 12 | TR |

TS = *S. lycopersicum* susceptible elite line
TR = *S. lycopersicum* resistant line
A = BC4F3 lines without the *S. habrochaites* (04TEP990312) introgression on the QTL BCT1.2
P = BC4F3 lines homozygous for the *S. habrochaites* (04TEP990312) introgression on the QTL BCT1.2

4.3.2 *Botrytis* strain BcT1:

| Duncan Grouping | Log10 | N | BCT9.1 |
|---|---|---|---|
| A | 1.68 | 12 | TS |
| A | 1.66 | 14 | A |
| B | 1.52 | 6 | P |
| C | 1.17 | 12 | TR |

TS = *S. lycopersicum* susceptible elite line
TR = *S. lycopersicum* resistant line
A = BC4F3 lines without the *S. habrochaites* (04TEP990312) introgression on the QTL BCT9.1
P = BC4F3 lines homozygous for the *S. habrochaites* (04TEP990312) introgression on the QTL BCT9.1

4.3.3 *Botrytis* strain BcT1:

| Duncan Grouping | Log10 | N | BCT1.2 |
|---|---|---|---|
| A | 1.72 | 12 | TS |
| B | 1.67 | 13 | A |
| C | 1.56 | 8 | P |
| D | 1.18 | 12 | TR |

TS = *S. lycopersicum* susceptible elite line
TR = *S. lycopersicum* resistant line
A = BC4F3 lines without the *S. habrochaites* (04TEP990312) introgression on the QTL BCT1.2
P = BC4F3 lines homozygous for the *S. habrochaites* (04TEP990312) introgression on the QTL BCT1.2

4.3.4 *Botrytis* strain BcT1:

| Duncan Grouping | Log10 | N | BCT9.1 |
|---|---|---|---|
| A | 1.72 | 12 | TS |
| B | 1.64 | 15 | A |
| C | 1.59 | 6 | P |
| D | 1.18 | 12 | TR |

TS = *S. lycopersicum* susceptible elite line
TR = *S. lycopersicum* resistant line
A = BC4F3 lines without the *S. habrochaites* (04TEP990312) introgression on the QTL BCT9.1
P = BC4F3 lines homozygous for the *S. habrochaites* (04TEP990312) introgression on the QTL BCT9.1

4.3.5 *Botrytis* strain BcT19:

| Duncan Grouping | Log10 | N | BCT1.2 |
|---|---|---|---|
| A | 1.74 | 12 | TS |
| B | 1.55 | 13 | A |
| C | 1.48 | 7 | P |
| D | 1.14 | 12 | TR |

TS = *S. lycopersicum* susceptible elite line
TR = *S. lycopersicum* resistant line
A = BC4F3 lines without the *S. habrochaites* (04TEP990312) introgression on the QTL BCT1.2
P = BC4F3 lines homozygous for the *S. habrochaites* (04TEP990312) introgression on the QTL BCT1.2

4.3.6 Botrytis strain BcT19:

| Duncan Grouping | Log10 | N | BCT9.1 |
|---|---|---|---|
| A | 1.74 | 12 | TS |
| B | 1.53 | 14 | A |
| B | 1.51 | 6 | P |
| C | 1.14 | 12 | TR |

TS = *S. lycopersicum* susceptible elite line
TR = *S. lycopersicum* resistant line
A = BC4F3 lines without the *S. habrochaites* (04TEP990312) introgression on the QTL BCT9.1
P = BC4F3 lines homozygous for the *S. habrochaites* (04TEP990312) introgression on the QTL BCT9.1

In the three independent experiments, there is a significant difference between lines with and without the *S. habrochaites* (04TEP990312) introgression on the QTL BCT1.2. Lines harbouring the *S. habrochaites* (04TEP990312) introgression on the QTL BcT1 showed a significant reduction of the necrosis length in comparison with lines without this introgression.

In the two independent experiments where lines have been challenged by the BcT1 strain, lines with the *S. habrochaites* (04TEP990312) introgression on the QTL BCT9.1 showed a significant reduction of the necrosis length in comparison with lines without this introgression. In the $3^{rd}$ experiment where lines have been challenged with the BcT19 strain, the experiment didn't show a significant difference between these lines for the QTL BCT9.1.

Deposit

The following seed sample of *Solanum habrochaites* 04TEP990312 was deposited with NCIMB, Ferguson Building, Craibstone Estate, Bucksburn, Aberdeen AB21 9YA, Scotland, UK on 21 May 2009 under the provisions of the Budapest Treaty in the name of Syngenta Participations AG:

| *Solanum habrochaites* seed line designation | Deposition date | Accession No |
|---|---|---|
| 04TEP990312 | 21 May 2009 | NCIMB 41623 |

TABLE 3

| Marker | chromosome | position | Primer F | SEQ ID | Primer R | SEQ ID |
|---|---|---|---|---|---|---|
| NT1293 | chr 6 | 33, 9 | GCTTCCATTTTGAAACAGC | SEQ ID NO: 1 | TAATCTTGCGACTGCTGAC | SEQ ID NO: 2 |
| NT3736 | chr 6 | 41, 3 | TCAAAATCAATTCAGAACACTC | SEQ ID NO: 3 | ACACTCGGGCTGAATCAC | SEQ ID NO: 4 |
| NT1597 | chr 1b | 39, 5 | GAAATATGTGATAAAACCTGCC | SEQ ID NO: 5 | TCCCACGGATTTAAAAGTG | SEQ ID NO: 6 |
| NT4636 | chr 1b | 56, 5 | TCAACTTGACCCACTTGTTC | SEQ ID NO: 7 | GAGGTGCTGGTACGATGG | SEQ ID NO: 8 |
| NT5734 | chr 9b | 0 | TTCTTCACTGTTGACAGAGAGAG | SEQ ID NO: 9 | CATTAGTTGAGAGTGATACCGC | SEQ ID NO: 10 |
| NT5921 | chr 9b | 12, 4 | CCACCATCATCATCACAATC | SEQ ID NO: 11 | AACGTGTTCCAATCACGAC | SEQ ID NO: 12 |

The invention claimed is:

1. A method for introgressing at least one allele associated with resistance to *Botrytis cinerea* at a quantitative trait locus contributing to resistance to *Botrytis cinerea* into a tomato plant lacking said allele, comprising:
   a) obtaining a first tomato plant which exhibits *Botrytis cinerea* resistance, wherein said resistance is associated with at least one QTL or a functional part thereof capable of directing or controlling expression of said resistance to *Botrytis cinerea*, wherein said QTL or a functional part thereof is genetically located on chromosome 6 between marker loci NT1293 and NT3736 as represented in Fig.2, which co-segregates with the *Botrytis* resistance trait and can be identified in a PCR reaction by at least two pairs of PCR oligonucleotide primers comprising:
      i. forward primer of SEQ ID NO: 1 and reverse primer of SEQ ID NO: 2, and
      ii. forward primer of SEQ ID NO: 3 and reverse primer of SEQ ID NO: 4;
   b) crossing said first tomato plant with a second tomato plant, wherein said second tomato plant lacks said allele; and
   c) identifying a plant resulting from the cross exhibiting increased resistance to *Botrytis cinerea* comprising detecting said QTL or a functional part thereof genetically located on chromosome 6 between marker loci NT1293 and NT3736 as represented in Fig.2 using oligonucleotides that are genetically linked to said QTL or functional part thereof on chromosome 6 between markers NT1293 and NT3736 and co-segregate with *Botrytis cinerea* resistance;
   d) optionally, isolating said plant; and
   e) optionally, back-crossing said plant with the first or second tomato plant.

2. A method for producing a tomato plant exhibiting resistance to *Botrytis cinerea*, comprising the steps of:
   a) selecting a plant of the genus Solanum, which exhibits *Botrytis cinerea* resistance, wherein said resistance is associated with at least one QTL or a functional part thereof capable of directing or controlling expression of said resistance to *Botrytis cinerea*, wherein said QTL or a functional part thereof is genetically located on chromosome 6 between marker loci NT1293 and NT3736 as represented in Fig.2, which co-segregates with the *Botrytis* resistance trait and can be identified in a PCR reaction by at least two pairs of PCR oligonucleotide primers comprising:
      i. forward primer of SEQ ID NO: 1 and reverse primer of SEQ ID NO: 2, and
      ii. forward primer of SEQ ID NO: 3 and reverse primer of SEQ ID NO: 4;
   b) crossing said plant of step a), which exhibits *Botrytis cinerea* resistance, with a tomato plant, which is susceptible to *Botrytis cinerea* or exhibits an intermediate level of resistance against *Botrytis cinerea* and
   c) selecting a progeny from said cross which exhibits *Botrytis* resistance comprising detecting said QTL or a functional part thereof genetically located on chromosome 6 between marker loci NT1293 and NT3736 as represented in Fig.2 using oligonucleotides that are genetically linked to said QTL or functional part thereof on chromosome 6 between markers NT1293 and NT3736 and co-segregate with *Botrytis cinerea* resistance.

3. A method for obtaining tomato fruits resistant to *Botrytis cinerea* comprising the steps of;
   a) selecting a plant of the genus *Solanum*, which exhibits *Botrytis cinerea* resistance, wherein said resistance is associated with at least one QTL or a functional part thereof capable of directing or controlling expression of said resistance to *Botrytis cinerea*, wherein said QTL or a functional part thereof is genetically located on chromosome 6 between marker loci NT1293and NT3736 as represented in Fig.2, which co-segregates with the *Botrytis* resistance trait and can be identified in a PCR reaction by at least two pairs of PCR oligonucleotide primers comprising:
      i. forward primer of SEQ ID NO: 1 and reverse primer of SEQ ID NO: 2, and
      ii. forward primer of SEQ ID NO: 3 and reverse primer of SEQ ID NO: 4 ;
   b)crossing said plant of step a), which exhibits *Botrytis cinerea* resistance, with a tomato plant, which is susceptible to *Botrytis cinerea* or exhibits an intermediate level of resistance against *Botrytis cinerea* ;
   [b] c) selecting a progeny plant from said cross which exhibits Botrytis resistance comprising detecting said QTL or a functional part thereof genetically located on chromosome 6 between marker loci NT1293 and NT3736 as represented in Fig.2 using oligonucleotides that are genetically linked to said QTL or functional part thereof on chromosome 6 between markers NT1293 and NT3736 and co-segregate with *Botrytis cinerea* resistance;
   [c] d) sowing a seed of the progeny plant of [b] c); and
   [d] e) growing said progeny plant in order to produce fruit and harvesting the fruits produced by said plant.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial sequence
<220> FEATURE:
<223> OTHER INFORMATION: Forward primer

<400> SEQUENCE: 1
gcttccattt tgaaacagc                19

<210> SEQ ID NO 2
<211> LENGTH: 19
<212> TYPE: DNA
<213> ORGANISM: Artificial sequence
<220> FEATURE:
<223> OTHER INFORMATION: Reverse primer

<400> SEQUENCE: 2
taatcttgcg actgctgac                19

<210> SEQ ID NO 3
<211> LENGTH: 22
<212> TYPE: DNA
<213> ORGANISM: Artificial sequence
<220> FEATURE:
<223> OTHER INFORMATION: Forward primer

<400> SEQUENCE: 3
tcaaaatcaa ttcagaacac tc            22

<210> SEQ ID NO 4
<211> LENGTH: 18
<212> TYPE: DNA
<213> ORGANISM: Artificial sequence
<220> FEATURE:
<223> OTHER INFORMATION: Reverse primer

<400> SEQUENCE: 4
acactcgggc tgaatcac                 18

<210> SEQ ID NO 5
<211> LENGTH: 22

```
<212> TYPE: DNA
<213> ORGANISM: Artificial sequence
<220> FEATURE:
<223> OTHER INFORMATION: Forward primer

<400> SEQUENCE: 5
gaaatatgtg ataaaacctg cc                                      22

<210> SEQ ID NO 6
<211> LENGTH: 19
<212> TYPE: DNA
<213> ORGANISM: Artificial sequence
<220> FEATURE:
<223> OTHER INFORMATION: Reverse primer

<400> SEQUENCE: 6
tcccacggat ttaaaagtg                                          19

<210> SEQ ID NO 7
<211> LENGTH: 20
<212> TYPE: DNA
<213> ORGANISM: Artificial sequence
<220> FEATURE:
<223> OTHER INFORMATION: Forward primer

<400> SEQUENCE: 7
tcaacttgac ccacttgttc                                         20

<210> SEQ ID NO 8
<211> LENGTH: 18
<212> TYPE: DNA
<213> ORGANISM: Artificial sequence
<220> FEATURE:
<223> OTHER INFORMATION: Reverse primer

<400> SEQUENCE: 8
gaggtgctgg tacgatgg                                           18

<210> SEQ ID NO 9
<211> LENGTH: 23
<212> TYPE: DNA
<213> ORGANISM: Artificial sequence
<220> FEATURE:
<223> OTHER INFORMATION: Forward primer

<400> SEQUENCE: 9
ttcttcactg ttgacagaga gag                                     23

<210> SEQ ID NO 10
<211> LENGTH: 22
<212> TYPE: DNA
<213> ORGANISM: Artificial sequence
<220> FEATURE:
<223> OTHER INFORMATION: Reverse primer

<400> SEQUENCE: 10
cattagttga gagtgatacc gc                                      22

<210> SEQ ID NO 11
<211> LENGTH: 20
<212> TYPE: DNA
<213> ORGANISM: Artificial sequence
<220> FEATURE:
<223> OTHER INFORMATION: Forward primer

<400> SEQUENCE: 11
```

```
ccaccatcat catcacaatc                                           20

<210> SEQ ID NO 12
<211> LENGTH: 19
<212> TYPE: DNA
<213> ORGANISM: Artificial sequence
<220> FEATURE:
<223> OTHER INFORMATION: Reverse primer

<400> SEQUENCE: 12
aacgtgttcc aatcacgac                                            19
```